United States Patent [19]

Rezai et al.

[11] Patent Number: 5,859,074
[45] Date of Patent: Jan. 12, 1999

[54] TREATING INTERPARTICLE BONDED AGGREGATES WITH LATEX TO INCREASE FLEXIBILITY OF POROUS, ABSORBENT MACROSTRUCTURES

[75] Inventors: Ebrahim Rezai, Motoyama-Kita Machi; Kesyin Hsueh, Kita-Ohgi; Motohiro Shimizu, Nishinomiya, all of Japan

[73] Assignee: The Procter & Gamble Co., Cincinnati, Ohio

[21] Appl. No.: 836,333

[22] PCT Filed: Oct. 30, 1995

[86] PCT No.: PCT/US95/13982

§ 371 Date: May 9, 1997

§ 102(e) Date: May 9, 1997

[87] PCT Pub. No.: WO96/14885

PCT Pub. Date: May 23, 1996

[30] Foreign Application Priority Data

Nov. 9, 1994 [AU] Australia ............... PM 9310

[51] Int. Cl.[6] ............... C08J 9/236; C08J 9/24
[52] U.S. Cl. .............. 521/54; 521/57; 521/64; 604/358; 604/367; 604/369
[58] Field of Search ............... 521/54, 57, 64; 604/358, 369, 367

[56] References Cited

U.S. PATENT DOCUMENTS

| | | | |
|---|---|---|---|
| 3,669,103 | 6/1972 | Harper et al. | 128/156 |
| 3,670,731 | 6/1972 | Harmon | 260/248 |
| 4,076,673 | 2/1978 | Burkholder | 260/29.2 EP |
| 4,410,571 | 10/1983 | Korpman | 427/385.5 |
| 4,861,539 | 8/1989 | Allen et al. | 264/204 |
| 5,102,597 | 4/1992 | Roe et al. | 264/126 |
| 5,124,188 | 6/1992 | Roe et al. | 428/72 |
| 5,149,344 | 9/1992 | Lahrman et al. | 55/167 |
| 5,324,561 | 6/1994 | Rezai | 428/72 |
| 5,372,766 | 12/1994 | Roe | 264/126 |

FOREIGN PATENT DOCUMENTS

| | | | |
|---|---|---|---|
| 91/15177 | 10/1991 | WIPO | A61F 13/15 |
| 91/15362 | 10/1991 | WIPO | B32B 3/10 |
| 94/07546 | 4/1994 | WIPO | A61L 15/60 |

*Primary Examiner*—Morton Foelak
*Attorney, Agent, or Firm*—Carl J. Roof; E. Kelly Linman; Jacobus C. Rasser

[57] ABSTRACT

Porous, absorbent macrostructures that comprise flexible interparticle bonded aggregates and are useful in absorbent articles such as diapers, adult incontinence pads, and sanitary napkins are disclosed. These porous macrostructures are treated with an effective amount of a latex to coat at least a portion of the particles comprising the bonded aggregate so as to impart increased flexibility to the macrostruture. This latex is capable of being sintered at a temperature of about 25° C. or lower, is at least somewhat hydrophilic when sintered, and has a Tg of about 25° C. or lower when sintered.

5 Claims, 4 Drawing Sheets

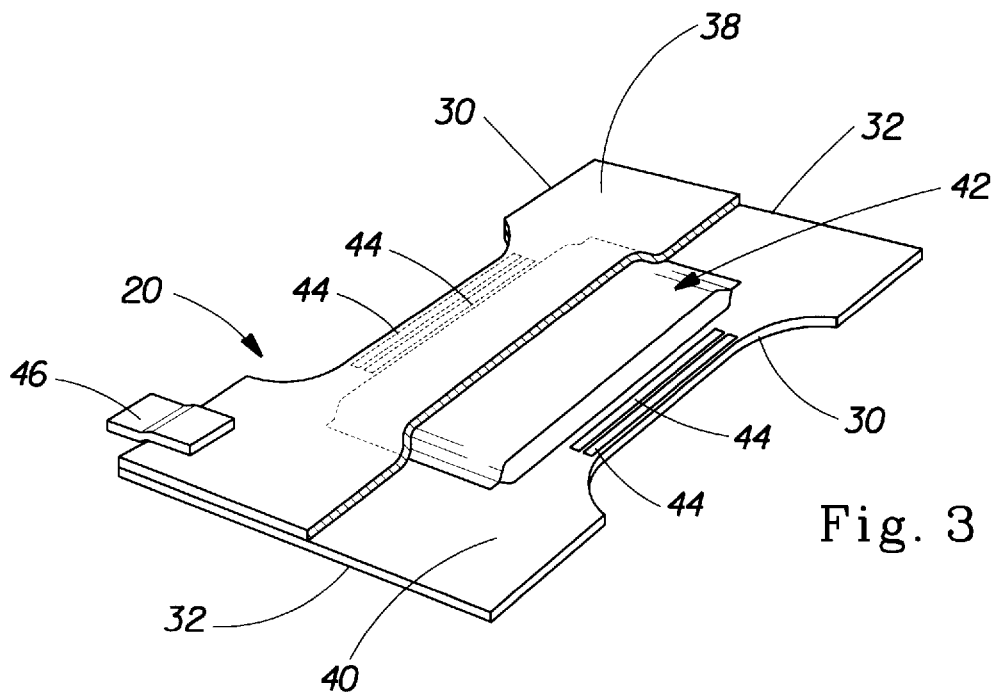
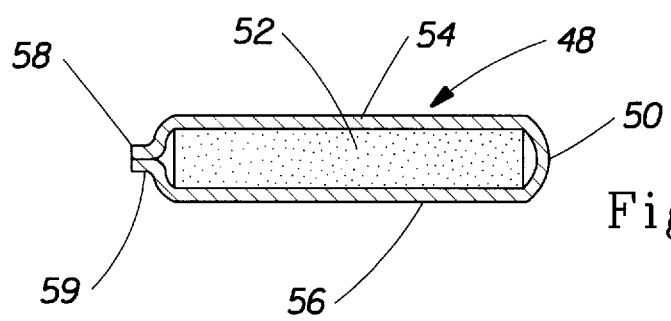
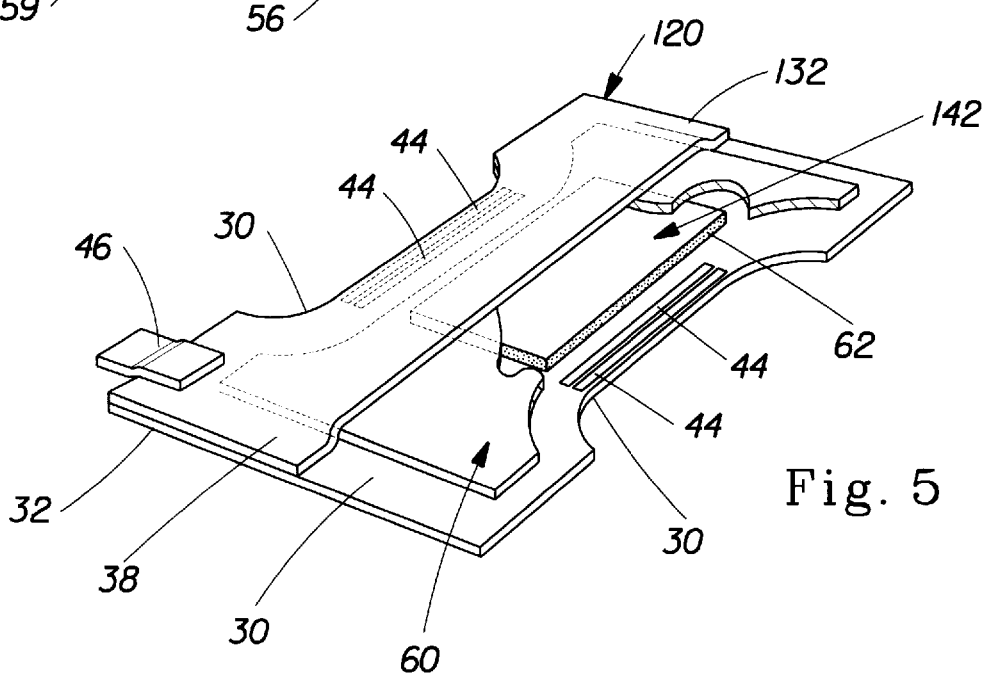

TREATING INTERPARTICLE BONDED AGGREGATES WITH LATEX TO INCREASE FLEXIBILITY OF POROUS, ABSORBENT MACROSTRUCTURES

FIELD OF THE INVENTION

This application relates to porous, absorbent macrostructures that comprise flexible interparticle bonded aggregates which are surface crosslinked. This application particularly relates to porous absorbent macrostructures in which an effective amount of latex is coated on a portion of the particles comprising the bonded aggregates so as to impart increased flexibility to the macrostructure.

BACKGROUND OF THE INVENTION

Particulate, absorbent, polymeric compositions are capable of absorbing large quantities of liquids such as water and body exudates (e.g., urine) and are further capable of retaining such absorbed liquids under moderate pressures. The absorption characteristics of such polymeric compositions make them especially useful for incorporation into absorbent articles such as diapers. See, for example, U.S. Pat. No. 3,699,103 (Harper et al), issued Jun. 13, 1972, and U.S. Pat. No. 3,770,731 (Harmon), issued Jun. 20, 1972, that disclose the use of particulate, absorbent, polymeric compositions (often referred to as "hydrogels", "superabsorbents", or "hydrocolloid materials") in absorbent articles.

Conventional particulate, absorbent, polymeric compositions, however, have the limitation that the particles are not immobilized and are free to migrate during processing and/or use. Migration of the particles can lead to material handling losses during manufacturing as well as nonhomogeneous incorporation of the particles into structures in which the particles are being used. A more significant problem, though, occurs when these particulate materials migrate during or after swelling in use. Such mobility leads to high resistance to liquid flow through the material due to the lack of stable interparticle capillary or liquid transport channels. This phenomenon is one form of what is commonly referred to as "gel blocking."

One attempt to overcome the performance limitations associated with absorbent particle mobility during use in absorbent articles is incorporation of the particulate, absorbent, polymeric compositions into tissue laminates, i.e. layered absorbent structures. By encapsulating the particles between tissue layers, the overall particle mobility within an absorbent structure is diminished. However, upon liquid contact, the particles within the laminate are often free to move relative to each other resulting in the breakdown of any pre-existent interparticle capillary channels.

Another attempted solution is to immobilize the particulate, absorbent, polymeric compositions by the addition of large quantities of liquid polyhydroxy compounds that act as an adhesive to hold the particles together or to a substrate. See, for example, U.S. Pat. No. 4,410,571 (Korpman), issued Oct. 18, 1983. While this approach does limit migration before and, to some extent, during swelling, the particles eventually become detached from each other in the presence of excess liquid, resulting again in the breakdown of any pre-existing capillary channels between the particles.

Another attempted solution to overcome the problem of absorbent particle mobility is to produce a superabsorbent film by extrusion of a solution of a linear absorbent polymer and subsequently crosslinking it. See, for example, U.S. Pat. No. 4,861,539 (Allen et al), issued Aug. 29, 1989 (crosslinked with a polyhydroxy compound such as a glycol or glycerol); and U.S. Pat. No. 4,076,673 (Burkholder), issued Feb. 28, 1978 (crosslinked with polyamine-polyamide epichlorohydrin adducts such as Kymene®). While these superabsorbent films may absorb significant quantities of liquids, they have limited liquid transport properties because they are essentially nonporous, i.e. lack internal capillary channels. Indeed, due to the lack of internal capillary channels, these superabsorbent films are especially prone to gel blocking.

Moreover, the crosslinking reaction between the hydroxy groups of the glycerol and the carboxy groups of the polymers present in the absorbent particles is relatively slow. Indeed, the glycerol treated absorbent particles are typically cured at 200° C. for 50 minutes. This provides relatively brittle sheets of bonded absorbent particles that are more difficult to handle, especially in making the ultimately desired absorbent structures. Accordingly, these brittle sheets need to be treated with a plasticizer, such as a mixture of water and glycerol, to make them relatively flexible and thus easier to handle in manufacturing absorbent structures.

U.S. Pat. No. 5,324,561 (Rezai et al), issued Jun. 23, 1994, discloses an improved porous aggregregate macrostructure where the absorbent particles are crosslinked with cationic amino-epichlorohydrin adducts, such as Kymene. The use of these cationic, preferably polymeric, amino-epichlorohydrin adducts as the crosslinking agent improves the cure rate and enhances the absorbent capacity of the particles by reducing or eliminating innerparticle crosslinking. In addition, the cationic functional (e.g., azetedinium) groups of these adducts are believed to react very rapidly with the carboxy functional groups of the polymer material comprising the absorbent particles, even at ambient room temperature, e.g., at 18°–25° C.).

Even crosslinking the absorbent particles with amino-epichlorohydrin adducts has been found not to solve all the problems of these porous aggregate macrostructures. One is the flexibility of the aggregate macrostructure, especially when its in the form of a sheet or strip. The absorbent particles that make up these aggregate macrostructures are inherently rigid and hard, thus causing inherent inflexibility. In addition, at low relative humidites (e.g., about 20%) typically encountered during winter months, these aggregate macrostructures tend to crack and break. These aggregates macrostructures also become more rigid when subjected to higher temperatures (i.e., at 50_C.) that typically occur during transport and storage of absorbent articles, such as diapers, in which these macrostructures are normally used. Such rigidity is undesirable in terms of the degree of comfort imparted to the wearer of absorbent article in which these macrostructures are contained.

Accordingly, it would be desirable to be able to make absorbent aggregate macrostructures of bonded absorbent particles that: (1) are more flexible; (2) impart a high degree of comfort to the wearer of the article; (3) do not tend to break or crack at low relative humidities typically encountered during winter months; (4) remain flexible even when subjected to higher temperatures typically encountered during transport and storage of absorbent articles, such as diapers; and (5) remain highly hydrophilic throughout transport, storage and use.

Briefly stated, the present invention meets the needs identifed above by providing porous absorbent macrostructures that comprise flexible interparticle bonded aggregates which are surface crosslinked. The porous absorbent macrostructures of the invention contain an effective amount of latex which is coated on a portion of the particles comprising the bonded aggregates so as to impart increased flexibility to the macrostructure.

In accordance with one aspect of the invention, a porous, absorbent, macrostructures that comprise flexible interparticle bonded aggregates is provided. These aggregates comprise: (a) a multiplicity of interconnected crosslinked particles comprising substantially water-insoluble, absorbent, hydrogel-forming polymer material; and (b) an effective amount of a latex to coat a portion of the particles so as to impart increased flexibility to the interparticle bonded aggregate. The latex is capable of being sintered at a temperature of about $25°$ C. or lower; it is at least somewhat hydrophilic when sintered; and it has a Tg of about $25°$ C. or lower when sintered.

In a preferred aspect of the invention, the interparticle bonded aggregate has pores between adjacent particles and the pores are interconnected by intercommunicating channels such that the macrostructure is liquid permeable, the circumscribed dry volume of the macrostructure being greater than about 0.008 mm$^3$. Another aspect of the invention envisions the preferred latex being an emulsified polymer produced from an olefinic monomer selected from the group consisting of $C_2$–$C_4$ alkyl and hydroxy alkyl acrylates, $C_1$–$C_4$ alkyl or hydroxy alkyl methacrylates and mixtures thereof.

In another aspect of the invention, a method for imparting improved flexibility to these porous absorbent macrostructures is provided. This method comprises the steps of: (a) treating the porous aggregate macrostructure with an effective amount of a latex to coat a portion of the particles of the porous aggregate macrostructure, wherein the latex is capable of being sintered at a temperature of about $25°$ C. or lower, is at least somewhat hydrophilic when sintered, and has a Tg of about $25°$ C. or lower when sintered; and (b) sintering the latex treated porous aggregate macrostructure at a temperature of about $25°$ C. or lower to impart increased flexibility thereto.

The porous, absorbent macrostructures obtained are useful, alone, or in combination with other absorbent materials, in absorbent structures for various absorbent articles, including diapers, adult incontinence pads, sanitary napkins, and the like. These porous absorbent macrostructures are more flexible and have greater stability at high temperature (e.g., about 50 C.) and low relative humidity (e.g., about 20% ). This is due to the inclusion of certain latexes that are believed to coat at least some of the particles of the macrostructure to provide an elastic shell. These latexes are also at least somewhat hydrophilic so as not to adversely affect the fluid handling properties of the macrostructure.

BRIEF DESCRIPTION OF THE DRAWINGS

FIG. 3 is a perspective view of a disposable diaper embodiment according to the present invention wherein portions of the topsheet have been cut-away to more clearly show the underlying absorbent core (an embodiment of an absorbent member according to the present invention) of the diaper wherein the absorbent member comprises a porous, absorbent macrostructure according to the present invention;

FIG. 4 is a cross-sectional view of the absorbent core of the diaper shown in FIG. 3 taken along sectional line 6—6 of FIG. 3; and FIG. 5 is a perspective view of a disposable diaper embodiment according to the present invention wherein portions of the topsheet have been cut away to more clearly show an alternative dual-layer absorbent core embodiment.

DETAILED DESCRIPTION OF THE INVENTION

I. Porous Absorbent Macrostructures

A. General Characteristics

Figure 1:
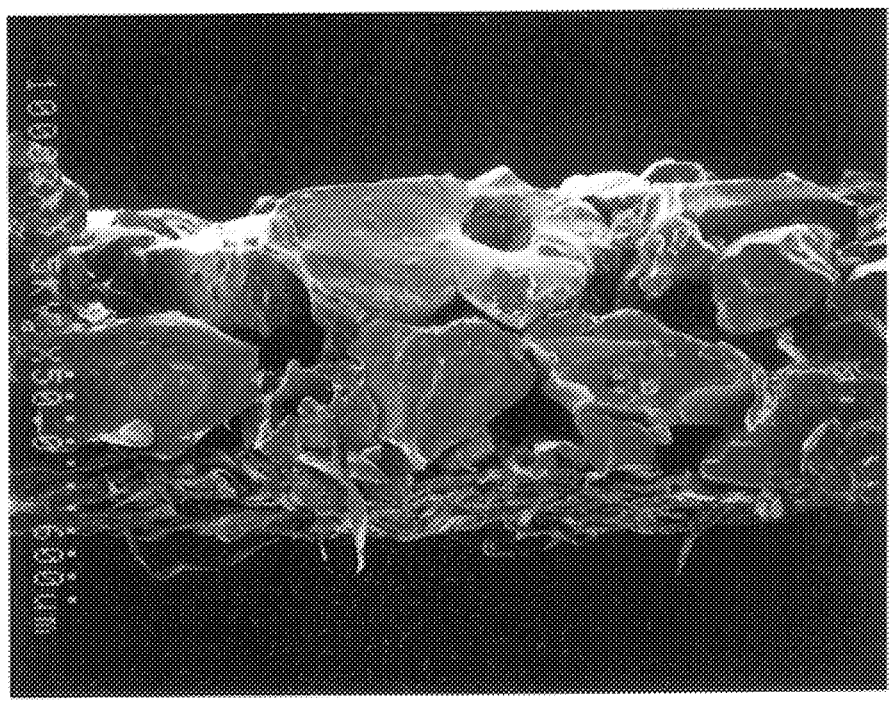
FIG. 1 is a photomicrograph (50× magnification) of a cross-section of a porous absorbent macrostructure without treatment with latex in accordance with the invention.
Figure 2:
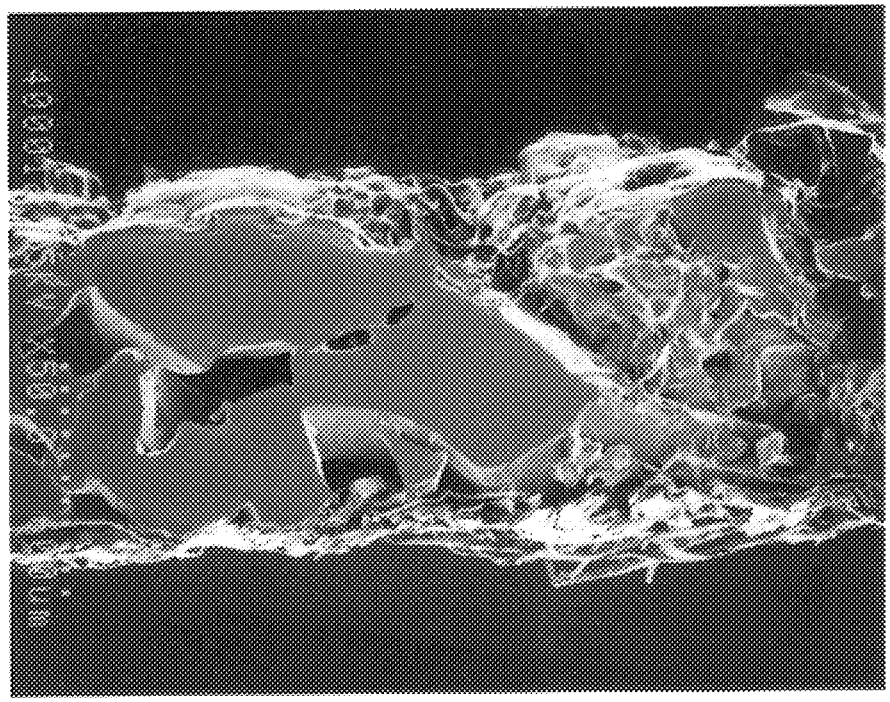
FIG. 2 is a photomicrograph (50× magnification) of the porous absorbent macrostructure depicted in FIG. 1 after being treated with a latex according to the invention.

Porous, absorbent macrostructures according to the present invention are structures capable of absorbing large quantities of liquids such as water and/or body exudates (e.g., urine or menses) and then retaining such liquids under moderate pressures. Because of the particulate nature of the precursor particles, the macrostructure has pores between adjacent precursor particles. These pores are interconnected by intercommunicating channels such that the macrostructure is liquid permeable (i.e., has capillary transport channels).

Due to the bonds formed between the precursor particles, the resultant aggregate macrostructure has improved structural integrity, increased liquid acquisition and distribution rates, and minimal gel-blocking characteristics. It has been found that when the macrostructure is contacted with liquids, the macrostructure swells generally isotropically even under moderate confining pressures, absorbs such liquids into the pores between the precursor particles, and then imbibes such liquids into the particles. The isotropic swelling of the macrostructure allows the precursor particles and the pores to maintain their relative geometry and spatial relationships even when swollen. Thus, the macrostructures are relatively "fluid stable" in that the precursor particles do not dissociate from each other, thereby minimizing the incidence of gel blocking and allowing the capillary channels to be maintained and enlarged when swollen so that the macrostructure can acquire and transport subsequent loadings of liquid, even excess liquid.

As used herein, the term "macrostructure" means a structure having a circumscribed volume when substantially dry (i.e., circumscribed dry volume) of at least about 0.008 mm$^3$, preferably at least about 10.0 mm$^3$, more preferably at least about 100 mm$^3$, most preferably at least about 500 mm$^3$. Typically, the macrostructures of the present invention will have a circumscribed dry volume much greater than about 500 mm$^3$. In preferred embodiments of the present invention, the macrostructures have a circumscribed dry volume of between about 1000 mm$^3$ and about 100,000 mm$^3$.

While the macrostructures of the present invention can have a number of shapes and sizes, they are typically in the form of sheets, films, cylinders, blocks, spheres, fibers, filaments, or other shaped elements. The macrostructures will generally have a thickness or diameter between about 0.2 mm and about 10.0 mm. Preferably for use in absorbent products, the macrostructures are in the form of a sheet. The term "sheet" as used herein describes macrostructures having a thickness at least about 0.2 mm. The sheets will preferably have a thickness between about 0.5 mm and about 10 mm, typically from about 0.5 mm to about 3 mm. Preferably, the sheet has a thickness of at least about 0.2 mm and a density of from about 0.5 to about 1.0 g/cc.

The porous, absorbent macrostructures of the present invention comprise interparticle bonded aggregates. These interparticle bonded aggregates usually comprise about 8 or more previously independent precursor particles. For preferred circumscribed dry volumes and sizes of the individual precursor particles used herein, these interparticle bonded aggregates typically are formed from about 100,000 or more individual precursor particles. These individual precursor particles can comprise granules, pulverulents, spheres, flakes, fibers, aggregates or agglomerates. The individual precursor particles can have a variety of shapes, such as cubic, rod-like, polyhedral, spherical, rounded, angular, irregular, randomly-sized irregular shapes, e.g., pulverulent products of grinding or pulverizing steps, or shapes having a large greatest dimension/smallest dimension ratio so as to be needle-like, flake-like, or fiber-like.

The interparticle bonded aggregate in the macrostructures of the present invention are formed, in essence, by the joining or adhering together of adjacent precursor particles. The adhesive agent is essentially the polymeric material that is present in the surface of these particles. When these precursor particles are treated with a crosslinking agent and physically associated, the polymer material present in the surface of these particles is sufficiently plastic and cohesive (e.g., sticky) such that adjacent particles are adhered together, typically as discrete linking portions between the particles. The crosslinking reaction between the particles then sets this adhered structure such that the particles in the aggregate remain cohesively bonded together.

B. Absorbent Precursor Particles

The macrostructures of the present invention are formed from polymer materials capable of absorbing large quantities of liquids. Such polymer materials are commonly referred to as "hydrogel", "hydrocolloid", or "superabsorbent" materials. The macrostructures preferably comprise substantially water-insoluble, absorbent hydrogel-forming, polymer material. The specific polymer materials will be discussed herein with respect to those forming the precursor particles.

Although the precursor particles can have a size varying over a wide range, specific particle size distributions and sizes are preferred. For purposes of the present invention, particle size is defined for precursor particles that do not have a large greatest dimension/smallest dimension ratio such as fibers (e.g., granules, flakes, or pulverulents) as the dimension of a precursor particle which is determined by sieve size analysis. For purposes of this invention, the mass average particle size of the precursor particles is important in determining the characteristics and properties of the resultant macrostructures. The mass average particle size of a given sample of precursor particles is defined as the particle size which is the average particle size of the sample on a mass basis. A method for determining the mass average particle size of a sample is described in the Test Methods section of U.S. Pat. No. 5,324,561 (Rezai et al), issued Jun. 23, 1994, which is incorporated by reference. The mass average particle size of the precursor particles will generally be from about 20 microns to about 1500 microns, more preferably from about 50 microns to about 1000 microns. In preferred embodiments of the present invention, the precursor particles have a mass average particle size less than about 1000 microns, more preferably less than about 600 microns, most preferably less than about 500 microns.

The particle size of materials having a large greatest dimension/smallest dimension such as fibers is typically defined by their largest dimension. For example, if absorbent, polymeric fibers (i.e. superabsorbent fibers) are used in the macrostructures of the present invention, the length of the fibers is used to define the "particle size." (The denier and/or the diameter of the fibers can also be specified.) In exemplary embodiments of the present invention, the fibers have a length greater than about 5 mm, preferably between about 10 mm and about 100 mm, more preferably between about 10 mm and about 50 mm.

The precursor particles comprise substantially water-insoluble, absorbent hydrogel-forming, polymer material having a multiplicity of anionic, functional groups, such as sulfonic acid, and more typically carboxy, groups. Examples of polymer materials suitable for use as the precursor particles herein include those which are prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof. See U.S. Pat. No. 5,324,561 (Rezai et al), issued Jun. 23, 1994 (herein incorporated by reference), which describes suitable precursor particles and their preparation.

Preferred polymer materials for use in the present invention contain carboxy groups. These polymers include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making the precursor particles are slightly network crosslinked polymers of partially neutralized polyacrylic acids and starch derivatives thereof. Most preferably, the precursor particles comprise from about 50 to about 95%, preferably about 75%, neutralized, slightly network crosslinked, polyacrylic acid (i.e. poly (sodium acrylate/acrylic acid)). Processes for network crosslinking the polymers and typical network crosslinking agents are described in greater detail in the hereinbefore-referenced U.S. Pat. No. 4,076,663.

The individual precursor particles can be formed in any conventional manner. Preferred methods for forming the precursor particles are those that involve aqueous solution or other solution polymerization methods. See, for example, U.S. Reissue Patent Re. 32,649 (Brandt et al), reissued Apr. 19, 1988. While it is preferred that the precursor particles be manufactured using an aqueous solution polymerization process, it is also possible to carry out the polymerization process using multi-phase polymerization processing techniques such as inverse emulsion polymerization or inverse suspension polymerization procedures. See U.S. Pat. No. 4,340,706 (Obayasashi et al), issued Jul. 20, 1982, U.S. Pat. No. 4,506,052 (Flesher et al), issued Mar. 19, 1985, and U.S. Pat. No. 4,735,987 (Morita et al), issued Apr. 5, 1988, all of which are incorporated by reference, for processes involving inverse suspension polymerization.

In preferred embodiments of the present invention, the precursor particles used to form the bonded particle aggregates are substantially dry. The term "substantially dry" is used herein to mean that the precursor particles have a liquid content, typically water or other solution content, less than about 50%, preferably less than about 20%, more preferably less than about 10%, by weight of the precursor particles. In general, the liquid content of the precursor particles is in the range of from about 0.01% to about 5% by weight of the precursor particles. The individual precursor particles can be dried by any conventional method such as by heating. Alternatively, when the precursor particles are formed using an aqueous reaction mixture, water can be removed from the reaction mixture by azeotropic distillation. The polymer-containing aqueous reaction mixture can also be treated with a dewatering solvent such as methanol. Combinations of these drying procedures can also be used. The dewatered mass of polymer material can then be chopped or pulverized to form substantially dry precursor particles of substantially water-insoluble, absorbent, hydrogel-forming, polymer material.

One preferred class of precursor particles useful in the present invention are those which exhibit a high absorptive capacity so that the resultant macrostructure formed from such precursor particles also has a high absorptive capacity. Absorptive capacity refers to the capacity of a given polymer material to absorb liquids with which it comes into contact. Absorptive capacity can vary significantly with the nature of the liquid being absorbed and with the manner in which the liquid contacts the polymer material. For purposes of this invention, Absorptive Capacity is defined in terms of the amount of Synthetic Urine absorbed by any given polymer material in terms of grams of Synthetic Urine per gram of polymer material in a procedure defined in the Test Methods section of U.S. Pat. No. 5,324,561 (Rezai et al), issued Jun. 23, 1994, which is incorporated by reference. Preferred precursor particles of having high absorptive capacity are those which have an Absorptive Capacity of at least about 20 grams, more preferably at least about 25 grams, of Synthetic Urine per gram of polymer material, more preferably at least about 35 grams, most preferably at least about 40 grams, of Synthetic Urine per gram of polymer. Typically, these higher fluid capacity precrsor particles have an Absorptive Capacity value of from about 25 to about 70 grams, more typically from about 35 to about 60 grams, most typically from about 40 to about 55 grams of Synthetic Urine per gram of polymer material. Typically, these high absorptive precursor particles have an Absorptive Capacity of from about 20 grams to about 70 grams of Synthetic Urine per gram of polymer material. Precursor particles having this relatively high absorptive capacity characteristic produce macrostructures that are especially useful in absorbent products, absorbent members, and absorbent articles since the resultant macrostructures formed from such precursor particles can, by definition, hold desirably high amounts of discharged body exudates such as urine.

The preferred processes for obtaining these precursor particles having relatively high Absorptive Capacity. As described in the above-referenced U.S. Pat. No. Reissue 32,649, aqueous solution polymerization involves the use of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. Suitable hydrogel-forming absorbent polymers having relatively high Absorptive Capacity include IM 1000 made by Hoechst Celanese, L74 made by Nippon Shokubai and F201 made by Nippon Gohsei.

Another preferred class of precursor particles useful in the present invention are those having relatively high Saline Flow Conductivity (SFC) values and relatively high Performance Under Pressure (PUP) capacity. See copending U.S. application Ser. No. 219,574 (Goldman et al), filed Mar. 29, 1994, which is incorporated by reference, where SFC values and PUP capacity are defined and methods for measuring these parameters are provided. Precursor particles useful in the present invention have SFC values of at least about $5\times10^{-7}$ cm$^3$sec/g, preferably at least about $10\times10^{-7}$ cm$^3$sec/g, and most preferably at least about $100\times10^{-7}$ cm$^3$sec/g. Typically, these SFC values are in the range of from about 30 to about $1000\times10^{-7}$ cm$^3$sec/g, more typically from about 50 to about $500\times10^{-7}$ cm$^3$sec/g, and most typically from about 100 to about $350\times10^{-7}$ cm$^3$sec/g. Precursor particles useful in the present invention generally have a PUP capacity at least about 23 g/g, preferably at least about 25 g/g, and most preferably at least about 29 g/g. Typically, these PUP capacity values are in the range of from about 23 to about 35 g/g, more typically from about 25 to about 33 g/g, and most typically from about 29 to about 33 g/g.

C. Mixtures of Precursor Particles Providing Improved Fluid Handling Properties

Additionally, macrostructures of the invention can be made from mixtures of precursor particles to minimize the potential problem of "gel blocking" without sacrificing desired fluid capacity. Mixtures can comprise precursor particles made from: (a) a first hydrogel-forming polymer having a relatively high Saline Flow Conductivity (SFC) value and relatively high Performance Under Pressure (PUP) capacity (for higher gel permeability/performance) a previously defined; and (b) a second hydrogel-forming polymer having a relatively high Absorptive Capacity. Generally, these mixtures comprise from about 50 to about 95% of the higher gel permeability/performance hydrogel-forming polymer and from about 5 to about 50% the higher fluid capacity hydrogel-forming polymer. Preferably, these mixtures comprise from about 50 to about 95% of the higher gel permeability/performance hydrogel-forming polymer and from about 5 to about 50% the higher fluid capacity hydrogel-forming polymer, more preferably from about 60 to about 95% of the higher gel permeability/performance hydrogel-forming polymer and from about 5 to about 40% the higher fluid capacity hydrogel-forming polymer, and most preferably from about 60 to about 80% of the higher gel permeability/performance hydrogel-forming polymer and from about 20 to about 40% the higher fluid capacity hydrogel-forming polymer.

The preferred processes for obtaining precursor particles having relatively high SFC and PUP capacity values involve surface crosslinking of the initially formed polymers. A number of processes for introducing surface crosslinks are disclosed in the art. These include those where: (i) a di- or poly-functional reagent(s) (e.g., glycerol, 1,3-dioxolan-2-one, polyvalent metal ions, polyquaternary amines) capable of reacting with existing functional groups within the hydrogel-forming absorbent polymer is applied to the surface of the hydrogel-forming absorbent polymer; (ii) a di- or poly-functional reagent that is capable of reacting with other added reagents and possibly existing functional groups within the hydrogel-forming absorbent polymer such as to increase the level of crosslinking at the surface is applied to the surface (e.g., the addition of monomer plus crosslinker and the initiation of a second polymerization reaction); (iii) no additional polyfunctional reagents are added, but additional reaction(s) is induced amongst existing components within the hydrogel-forming absorbent polymer either during or after the primary polymerization process such as to generate a higher level of crosslinking at or near the surface (e.g., heating to induce the formation of anhydride and or esters crosslinks between existing polymer carboxylic acid and/or hydroxyl groups and suspension polymerization processes wherein the crosslinker is inherently present at higher levels near the surface); and (iv) other materials are added to the surface such as to induce a higher level of crosslinking or otherwise reduce the surface deformability of the resultant hydrogel. Combinations of these surface crosslinking processes either concurrently or in sequence can also be employed. In addition to crosslinking reagents, other components can be added to the surface to aid/control the distribution of crosslinking (e.g., the spreading and penetration of the surface crosslinking reagents.) See copending U.S. application Ser. No. 219,574 (Goldman et al), filed Mar. 29, 1994, which is incorporated by reference.

Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992; all of which are incorporated by reference. See also copending U.S. application Ser. No. 219,574 (Goldman et al), filed Mar. 29, 1994, which is incorporated by reference, and especially Examples 1 to 4. Suitable hydrogel-forming absorbent polymers having relatively high SFC and PUP capacity values include L761f made by Nippon Shokubai, SXP made by Chemische Fabrik Stockhausen, XZ made by Dow Chemical and XP-30 made by Nalco Chemical.

Precursor particles useful in the present invention that have a relatively high Absorptive Capacity and a relatively high Absorption (AAP) value are disclosed in the U.S. Pat. No. 4,076,663 (Matsuda et al), issued Feb. 28, 178, U.S. Reissue Patent 32,649 (Brandt et al), reissued Apr. 19, 1988, U.S. Pat. No. 4,625,001 (Tsubakimoto et al), issued Nov. 25, 1986, U.S. Pat. No. 4,666,983 (Tsubakimoto et al), issued May 19, 1987, U.S. Pat. No. 4,734,478 (Tsubakimoto et al), issued Mar. 29, 1988, U.S. Pat. No. 4,735,987 (Morita et al), issued Apr. 5, 1988, U.S. Pat. No. 4,973,632 (Nagasuna et al), issued Nov. 27, 1990, U.S. Pat. No. 5,264,471 (Chmelir), issued Nov. 23, 1993 and Europeant Patent Application 530,438 (Chambers et al), published Mar. 10, 1993, all of which are incorporated by reference. "Absorptive Capacity" refers to the capacity of a given polymer material to absorb fluids with which it comes into contact and can vary significantly with the nature of the fluid being absorbed and with the manner in which the liquid contacts the polymer material. For purposes of this invention, Absorptive Capacity is defined in terms of the amount of Synthetic Urine absorbed by any given polymer material in terms of grams of Synthetic Urine per gram of polymer material. See Test Methods section hereafter.

These higher fluid capacity precursor particles have Absorptive Capacity values of at least about 25 grams, more preferably at least about 35 grams, most preferably at least about 40 grams, of Synthetic Urine per gram of polymer. Typically, these higher fluid capacity precursor particles have an Absorptive Capacity value of from about 25 to about 70 grams, more typically from about 35 to 60 grams, most typically from about 40 to about 55 grams of Synthetic Urine per gram of polymer material.

The preferred processes for obtaining these precursor particles having relatively high Absorptive Capacity. As described in the above-referenced U.S. Pat. No. Reissue 32,649, aqueous solution polymerization involves the use of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. Suitable hydrogel-forming absorbent polymers having relatively high Absorptive Capacity include IM 1000 made by Hoechst Celanese, L74 made by Nippon Shokubai and F201 made by Nippon Gohsei.

Mixtures according to variant (2) of the present invention comprise precursor particles made from: (a) a first hydrogel-forming polymer in the form of spherical shaped particles or spherical shape agglomerates of particles; and (b) a second hydrogel-forming polymer in the form of nonspherical or irregular shaped particles. The first hydrogel-forming polymer has a higher fluid capacity than the second, while the second hydrogel-forming polymer has a higher PUP capacity than the first polymer. It is believed the reason that macrostructures made exclusively from spherical shaped particles or agglomerates of hydrogel-forming absorbent polymer are prone to gel block is due to the formation of close, compacted structure that would have poorer fluid permeability. It has been found that the inclusion of non-spherical (irregular) shaped particles seems to perturb the self-assembling nature of the spherical shaped particles or agglomerates thereof during the making of the macrostructures, especially macrostructures in sheet form. As a result, the macrostructure is no longer prone to blocking fluid.

Generally, these mixtures according to variant (2) comprise from about 5 to about 50% of the spherical precursor particles or agglomerates thereof which have high fluid capacity and from about 50 to about 95% the nonspherical or irregular particles which have higher PUP capacity than the spherical precursor particles. Preferably, these mixtures comprise from about 10 to about 50% of the spherical particles and from about 50 to about 90% the nonspherical particles, and most preferably from about 20 to about 40% of the spherical particles and from about 60 to about 80% the nonspherical particles.

Spherical shaped particles can be obtained by multi-phase polymerization processing techniques such as inverse emulsion polymerization or inverse suspension polymerization procedures. In the inverse emulsion polymerization or inverse suspension polymerization procedures, the aqueous reaction mixture is suspended in the form of tiny droplets in a matrix of a water-immiscible, inert organic solvent such as cyclohexane. The resultant precursor particles are generally spherical in shape. Inverse suspension polymerization procedures are disclosed in U.S. Pat. No. 4,093,776 (Aoki et al), issued Jun. 6, 1978, U.S. Pat. No. 4,340,706 (Obaysashi et al), issued Jul. 20, 1982, U.S. Pat. No. 4,446,261 (Yamasaki et al), issued, U.S. Pat. No. 4,506,052 (Flesher et al), issued Mar. 19, 1985, U.S. Pat. No. 4,541,871 (Obayashi et al), issued Sep. 17, 1985, U.S. Pat. No. 4,698,414 (Cramm et al), issued Oct. 6, 1987, U.S. Pat. No. 4,735,987 (Morita et al), issued Apr. 5, 1988, U.S. Pat. No. 4,833,179 (Young et al), issued May 23, 1989, and European Patent Application 522,570, published Jan. 13, 1993, all of which are incorporated by reference. Suitable spherical shaped particles of hydrogel-forming absorbent polymer include F201 made by Nippon Gohsei and Base 60 made by Mitsubishi Chemical.

Nonspherical shaped particles can be obtained by bulk polymerization procedures including aqueous solution or other solution polymerization methods. As described in the above-referenced U.S. Reissue Patent 32,649, aqueous solution polymerization involves the use of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. The mass of polymer material thereby formed is then pulverized or chopped to form the individual precursor particles. Suitable nonspherical shaped particles of hydrogel-forming absorbent polymer include L761f made by Nippon Shokubai, SXP or SXM made by Chemische Fabrik Stockhausen, and 1180 or XP 30 made by Nalco Chemical.

C. Crosslinking Agents

In preparing macrostructures according to the present invention, a crosslinking agent is used to provide crosslinking at the surface of the absorbent precursor particles. This typically occurs as a result of the crosslinking agent by reacting with the polymer material in these particles. Typically, the polymer material of the absorbent precursor particles has anionic, and preferably carboxy, functional groups that form a covalent, ester-type bond with the crosslinking agent. These portions of the absorbent particle that have been effectively crosslinked will swell less in the presence of aqueous (body) fluids relative to the other uncrosslinked portions of the particle.

Suitable crosslinking agents for this purpose can be nonionic and possess at least two functional groups per molecule capable of reacting with the carboxy group. See, for example, U.S. Pat. No. 5,102,597 (Roe et al), issued Apr. 7, 1992, which is incorporated by reference, and which discloses a variety of nonionic crosslinking agents that include polyhydric alcohols such as ethylene glycol, diethylene glycol, triethylene glycol, tetraethylene glycol, polyethylene glycol, glycerol (1, 2, 3-propanetriol), polyglycerol, propylene glycol, 1, 2-propanediol, 1, 3-propanediol, trimethylol propane, diethanolamine, triethanolamine, polyoxypropylene oxyethylene-oxypropyle block copolymer, sorbitan fatty acid esters, polyexyethylene sorbitan fatty acid esters, pentaerythritol, and sorbitol; polyglycidyl ether compounds such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether, and propylene glycol diglycidyl ether; polyaziridine compounds such as 2, 2-bishydroxymethyl butanol-tris[3-(i-aziridine) propionate], 1, 6-hexamethyl tolulene diethylene urea, and diphenyl methane-bis-4, 4'-N,N'-diethylene urea; haloepoxy compounds such as epichlorohydrin and a-methylfluorohydrin; polyaldehyde compounds such as glutaraldehyde and glyoxazole; polyamine compounds such as ethylene diamine, diethylene triamine, triethylene tetramine, tetraethylene pentamine, pentaethylene hexamine, and polyethylene imine; and polyisocyanate compounds such as 2, 4-tolulene diisocyanate and hexamethylene diisocyanate. The particularly preferred nonionic crosslinking agent is glycerol.

A preferred crosslinking agent for use in the present invention is an adduct of epichlorohydrin with certain types of monomeric or polymeric amines. See U.S. Pat. No. 5,324,561 (Rezai et al), issued Jun. 23, 1994, which is incorporated by reference and which discloses suitable cationic amino-epichlorohydrin adduct crosslinking agents. These amino-epichlorohydrin adducts, and especially the polymeric resin versions of these adducts, are preferred crosslinking agents because they react only with the polymer material at the surface precursor particles. In addition, the cationic functional groups (e.g., azetedinium groups) of these adducts, particularly polymeric resin versions, are believed to react very rapidly with the anionic, typically carboxy, functional groups of the polymer material of the absorbent particles, even at room temperature (e.g., at from about 18° to about 25° C.). As a result, fairly modest levels (e.g., as low as about 1% by weight of the particles) of these amino-epichlorohydrin adducts are required to provide effective surface crosslinking of the polymer material present in the absorbent precursor particles.

Suitable cationic amino-epichorohydrin adducts useful as crosslinking agents include those where ephichlorohydrin are reacted with monomeric di-, tri- and higher amines having primary or secondary amino groups in their structure such as bis-2-aminoethyl ether, N,N-dimethylethylenediamine, piperazine, ethylenediamine, N-amninoethyl piperazine, and dialkylene triamines such as diethylenetriamine, and dipropylenetriamine; polymeric amines such as polyethyleneimines, and certain polyamidepolyamines derived from polyalkylene polyamines and saturated $C_3$–$C_{10}$ dibasic carboxylic acids. These epichlorohydrin/polyamide-polyamine adducts are well known in the art as wet strength resins for paper products. The most preferred epichlorohydrin/polyamide-polyamine adducts are those derived from the polyethylene polyamines containing from two to four ethylene groups, two primary amine groups, and from one to three secondary amine groups, and saturated aliphatic $C_3$–$C_{10}$ dicarboxylic acids, most preferrably those containing from 3 to 8 carbon atoms, such as malonic, succinic, glutaric, adipic, together with diglycolic acid. Cationic polyamide-polyamine-epichlorohydrin resins particularly preferred for use herein as crosslinking agents are commercially marketed by Hercules Inc. under the trade name Kymene®. Especially useful are Kymene® 557H, Kymene® 557LX and Kymene® 557 Plus, which are the epichlorohydrin adducts of polyamide-polyamines which are the reaction products of diethylenetriamine and adipic acid. They are typically marketed in the form of aqueous solutions of the cationic resin material containing from about 10% to about 33% by weight of the resin active.

D. Preparation of Interparticle Bonded Aggregates and Macrostructures

In preparing the interparticle bonded aggregates that comprise the porous, absorbent macrostructures, the absorbent precursor particles are treated with an sufficient amount of the crosslinking agent to react with the polymer material at the surface of the particles so as to cause effective crosslinking, i.e., the crosslinked surface of the particle swells less in the presence of aqueous body fluids relative to the uncrosslinked portions. What constitutes "a sufficient amount" of the crosslinking depends upon a number of factors, including the particular absorbent precursor particles treated, the crosslinking agent used, the particular effects desired in forming the interparticle bonded aggregate, and like factors. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents), which are incorporated by reference.

Besides the absorbent precursor particles and the crosslinking agent, other components or agents can be used as aids in preparing the interparticle bonded aggregates. For example, water is typically used with the crosslinking agent to form an aqueous treatment solution thereof. Water promotes the uniform dispersion of the crosslinking agent on the surface of the precursor particles and causes permeation of the crosslinking agent into the surface regions of these particles. Water also promotes a stronger physical association between the treated precursor particles, providing greater integrity of the resultant interparticle bonded crosslinked aggregates. The actual amount of water used can vary depending upon the type of crosslinking agent used, the type of polymer material used in forming the precursor particles, the particle size of these precursor particles, the inclusion of other optional components (e.g., glycerol) and like factors. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents), which are incorporated by reference.

Although not absolutely necessary, organic solvents can be used, usually to promote uniform dispersion of the crosslinking agent onto the surface of the precursor particles. These organic solvents are typically hydrophilic, and can include lower alcohols such as methanol and ethanol; amides such as N,N-dimethylformamide and N,N-diethylformamide; and sulfoxides such as dimethylsulfoxide. The actual amount of hydrophilic solvent used can vary depending upon the adduct used, the polymer material used forming the precursor particles, the particle size of these precursor particles and like factors. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents), which are incorporated by reference.

Other optional components can also be used with the crosslinking agent, and especially aqueous treatment solutions thereof. It is particularly preferred that the treatment solution include a plasticizer to facilitate crosslinking, especially when cationic amino-epichlorohydrin adducts are used as the crosslinking agent. See U.S. Pat. No. 5,324,561 (Rezai et al), issued Jun. 23, 1994 which is incorporated by reference. Suitable plasticizers include water, alone or in combination with other components such as glycerol, propylene glycol (i.e. 1,2-propanediol), 1,3-propanediol, ethylene glycol, sorbitol, sucrose, polymeric solutions such as those involving polyvinyl alcohol, ester precursors of polyvinyl alcohol, or polyethylene glycol, or mixtures thereof. These other components in the plasticizer, such as glycerol, are believed to act as humectants, coplasticizers or both, with water being the primary plasticizer. The preferred plasticizer for use in the present invention is a mixture of glycerol and water, particularly when included as part of an aqueous treatment solution of the cationic amino-epichlorohydrin adduct, in a weight ratio of glycerol to water of from about 0.5:1 to about 2:1, preferably from about 0.8:1 to about 1.7:1.

The actual amount of plasticizer used can vary depending upon the particular plasticizer used, the type of polymer material used in forming the precursor particles, and the particular flexibility effects desired from the plasticizer. Typically, the plasticizer is used in an amount of from about 5 to about 100 parts by weight, preferably from about 5 to about 60 parts by weight, more preferably from about 10 to about 30 parts by weight, most preferably from about 15 to about 20 parts by weight, per 100 parts by weight of the precursor particles. See U.S. Pat. No. 5,324,561 (Rezai et al), issued Jun. 23, 1994, which is incorporated by reference.

In the method of the present invention, the absorbent precrsor particles can be treated with the cationic amino-epichlorohydrin adduct, typically an aqueous solution thereof, by any of a variety of techniques. These include any method for applying solutions to materials, including coating, dumping, pouring, dropping, spraying, atomizing, condensing, or immersing the absorbent precursor particles with the cationic amino-epichlorohydrin adduct, or solution thereof. As used herein, the term "applied" means that at least a portion of the surface area of at least some of the precursor particles to be bonded together has an effective amount of the adduct on it to cause surface crosslinking. In other words, the cationic adduct can be applied onto some of the precursor particles, all of the precursor particles, a portion of the surface of some or all of the precursor particles, or the entire surface of some or all of the precursor particles. Preferably, the adduct is coated onto the entire surface of most, preferably all, of the absorbent precursor particles so as to enhance the efficiency, strength, and density of the interparticle bonds between the precursor particles, as well as the desired surface crosslinking of the polymer material in the surface of these precursor particles.

After the treatment solution has been applied onto the precursor particles, the treated precursor particles can be mixed or layered together by any of a number of mixing or layering techniques to insure that the precursor particles are thoroughly coated with the treatment solution. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents), which are incorporated by reference. Before, during, or after applying the treatment solution, the precursor particles are physically associated together to form an aggregate macrostructure. The precursor particles are preferably physically associated together by applying an associating agent onto the precursor particles and physically contacting the precursor particles at least the portion of the surface of the precursor particles having the associating agent applied thereto. Associating agents useful in the present invention include hydrophilic organic solvents, typically low molecular weight alcohols such as methanol or ethanol; water, a mixture of hydrophilic organic solvents and water, the crosslinking agents, or mixtures thereof. Preferred associating agents are water, methanol, ethanol, cationic polymeric amino-epichlorohydrin resins such as Kymene® 557H, or 557LX or Plus, or mixtures thereof. Typically the associating agent comprises a mixture including the crosslinking agent such that the step of applying the crosslinking is carried out simultaneously with the step of applying the associating agent.

The associating agents can be applied to the precursor particles by any of various techniques and apparatus used for applying solutions to materials including coating, dumping, pouring, spraying, atomizing, condensing, or immersing the associating agent on the precursor particles. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents), which are incorporated by reference. When an associating agent has been applied to the precursor particles, the precursor particles can be physically contacted together in a number of different ways. For example, the associating agent alone can hold the particles together in contact. Alternatively, gravitational forces can be used to insure contact between the precursor particles, e.g., by layering precursor particles. Further, the particles can be placed in a container having a fixed volume so as to insure contact between the precursor particles.

The precusor particles can alternatively be physically associated together by physically constraining the precursor particles such that they are in contact with each other. For example, the precursor particles can be packed tightly into a container having a fixed volume such that the precursor particles physically contact each other. Alternatively or in combination with the above procedure, gravitational forces (e.g., layering) can be used to physically associate the precursor particles. The precursor particles can also be physically associated together by electrostatic attraction or by the introduction of an adhering agent (e.g., an adhesive material such as a water-soluble adhesive) to adhere them together. The precursor particles can also be attached to a third member (a substrate) such that the precursor particles are brought into contact with each other by the substrate.

In an alternative method of forming the macrostructures of the present invention, the aggregate of the precursor particles is shaped into various geometries, spatial relationships, and densities to form an aggregate having a defined shape, size, and/or density. The aggregate can be shaped by any conventional shaping techniques as are known in the art. Preferred methods for shaping the aggregate include casting, molding, or forming operations. Casting and molding techniques generally involve introducing the precursor particles into a prepared mold cavity and applying pressure to (compressing) the aggregate to cause the aggregate to conform to the shape of the mold cavity. Examples of specific molding techniques for use herein include compression molding, injection molding, extrusion or laminating. For example, a multiplicity of precursor particles can be added to a container having a fixed volume mold cavity and the aggregate compressed to conform to the shape of the mold cavity so that the resultant macrostructure has the same shape. Forming techniques involve performing various operations on the aggregate to modify its shape, and/or size, and/or density. Examples of specific forming techniques for use herein include rolling, forging, extruding, spinning, coating or drawing operations. For example, an aggregate mixture of the precursor particles and at least the cationic amino-epichlorohydrin adduct can be passed between a pair of compaction rolls to form an aggregate sheet. Alternatively, the aggregate mixture can be extruded through an orifice to form an aggregate having a shape corresponding to that of the orifice. Further, the aggregate mixture can be cast on a surface to form an aggregate having a desired shape or surface morphology. Any or all of these techniques can also be used in combination to form the shaped aggregate. Any suitable apparatus as are known in the art can be used to carry out such operations, which can be performed with the material or portions of the apparatus either hot and/or cold. A preferred method and apparatus for continuously forming the aggregate macrostructures of the present invention into sheets is described in U.S. Pat. No. 5,324,561 (Rezai et al), issued Jun. 23, 1994 (cationic amino-epichlorohydrin adduct crosslinking agents), which are incorporated by reference. See especially FIG. 9 from this patent and its associated description. Such sheets can include a plurality of voids or slits so as to increase the flexibility of the sheet. Various embodiments of such slits are described in copending U.S. application Ser. No. 08/142,258 (Hseuh et al), filed Oct. 22, 1993; copending U.S. application Ser. No. 08/142,259 (Rezai et al), filed Oct. 22, 1993; and copending U.S. application Ser. No. 08/142,629 (Dierckes et al), filed Oct. 22, 1993, all of which are incorporated herein by reference.

Simultaneously or after the treatment solution has been applied, the precursor particles have been physically associated together to form an aggregate, and the aggregate has been shaped, the crosslinking agent is reacted with the polymer material of the precursor particles, while maintaining the physical association of the precursor particles, to provide effective surface crosslinking in the precursor particles in the aggregate macrostructure. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents), which are incorporated by reference. Because of the relatively reactive cationic functional groups of the amino-epichlorohydrin adducts that can be used as crosslinking agents in the present invention, this crosslinking reaction can occur at relatively low temperatures, including ambient room temperatures. Such ambient temperature curing is particularly desirable when the treatment solution additionally contains a plasticizer, such as a mixture of water and glycerol. Curing at significantly above ambient temperatures can cause the plasticizer to be driven off due to its volatility, thus necessitating an additional step to plasticize the resulting interparticle bonded aggregate. Such ambient curing is typically carried out at a temperature of from about 18 to about 35° C. for from about 12 to about 48 hours. Preferably, such ambient curing is carried out at a temperature of from about 18 to about 25° C. for from about 24 to about 48 hours.

Although the crosslinking reaction can occur at ambient temperatures, such curing can also be carried out at higher temperatures to speed up the reaction. Higher temperature curing typically involves heating the treated and associated precursor particles to cause the crosslinking reaction to occur in a shorter period of time, typically minutes. This heating step can be carried out using a number of conventional heating devices, including various ovens or dryers well known in the art.

Generally, heat curing can be carried out at a temperature above about 50° C. for a period of time sufficient to complete the crosslinking reaction. The particular temperatures and times used in heat curing will depend upon the particular crosslinking agents used and the polymer material present in the precursor particles. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents), which are incorporated by reference. In the case of the preferred cationic amino-epichlorohydrin adducts, heat curing is generally carried out at a temperature in the range of from about 50 to about 205° C. for from about 1 to about 20 minutes. Preferably, heat curing is carried out at a temperature of from about 180 to about 200° C. for from about 5 to about 15 minutes.

The physical association of the treated precursor particles needs to be maintained during the curing step so that, as crosslinking occurs, adjacent precursor particles become cohesively bonded together. If forces or stresses are sufficient to disassociate the precursor particles that are present during the crosslinking reaction, insufficient bonding of the precursor particles can occur. This can result in aggregates having poor structural integrity. The physical association of the precursor particles is typically maintained by insuring minimal dissociation forces or stresses are introduced during the curing step.

The steps for producing the macrostructures need not be carried out in any specific order, and can be carried out simultaneously. For example, the treatment solution can be applied simultaneously with the physical association of the precursor particles, shaped into a preferred shape and typically a desired density, and then the crosslinking agent reacted with the polymer material of the precursor particles, either immediately after the above steps are completed or after the aggregate has been left standing for a period of time, to simultaneously surface crosslink the precursor particles and form the aggregate macrostructure. Typically, the precursor particles are mixed or sprayed with a solution of the crosslinking agent, water, a humectant and/or coplasticizer (e.g., glycerol), and a hydrophilic organic solvent (e.g., methanol) to form an adhered together aggregate. The adhered aggregate (i.e. the associated precursor particles and the aqueous mixture) is subsequently shaped into a densified sheet by a combination of extruding and rolling techniques as described above. The crosslinking agent is subsequently reacted with the polymer material by ambient or heat curing to simultaneously cause crosslinking at the surface of the precrsor particles and to form a cohesive interparticle bonded aggregate macrostructure.

The macrostructures can be also be treated with a plasticizer after curing to effect surface crosslinking. Suitable plasticizers include water, alone or in combination with the humectants/coplasticizers previously described, preferably glycerol. The plasticizer can be applied to the macrostructures in a number of different ways, including spraying, coating, atomizing, immersing, or dumping the plasticizer onto the macrostructure. Alternatively, in the case of water alone, the macrostructure can be placed in a high humidity environment (e.g., greater than 70% relative humidity). The amount of plasticizer applied to the macrostructure can be selected depending upon the specific plasticizer used, and the effects desired. Typically, the amount of plasticizer applied is from about 5 to about 100 parts by weight, preferably from about 5 to about 60 parts by weight, per 100 parts by weight of the macrostructure. A particularly preferred plasticizer comprises a mixture of glycerol and water in a weight ratio of from about 0.5:1 to about 2:1, preferably from about 0.8:1 to about 1.7:1.

Various types of fiber material can be used as the reinforcing members in the macrostructures of the present invention. Any type of fiber material which is suitable for use in conventional absorbent products is also suitable for use in the macrostructures herein. Specific examples of such fiber material include cellulose fibers, modified cellulose fibers, rayon, polypropylene, and polyester fibers such as polyethylene terephthalate (DACRON), hydrophilic nylon (HYDROFIL), and the like. Examples of other fiber materials for use in the present invention in addition to some already discussed are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the macrostructures of the present invention by virtue of their good wicking properties. This is because, in the macrostructures herein, the wicking propensity of the fibers is as important, if not more important, than the absorbent capacity of the fiber material itself due to the high rate of fluid uptake and lack of gel blocking properties of the macrostructures of the present invention. Synthetic fibers are generally preferred for use herein as the fiber component of the macrostructure. Most preferred are polyolefin fibers, preferably polyethylene fibers.

Other cellulosic fiber materials which can be useful in certain macrostructures herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Suitable stiffened, twisted, curled cellulose fibers useful as the hydrophilic fiber material herein are described in greater detail in U.S. Pat. No. 4,888,093 (Dean et al), issued Dec. 19, 1989; U.S. Pat. No. 4,889,595 (Herron et al), issued Dec. 26, 1989; U.S. Pat. No. 4,889,596 (Schoggen et al), issued Dec. 26, 1989; U.S. Pat. No. 4,889,597 (Bourbon et al), issued Dec. 26, 1989; and U.S. Pat. No. 4,898,647 (Moore et al), issued Feb. 6, 1990, all of which are incorporated by reference.

As used herein, the term "hydrophilic" describes fibers or the surfaces of fibers which are wetted by the liquids deposited onto the fibers (i.e., if water or aqueous body fluid readily spreads on or over the surface of the fiber without regard to whether or not the fiber actually imbibes fluid or forms a gel). The state of the art respecting wetting of materials allows definition of hydrophobicity (and wetting) in terms of contact angles and the surface tension of the liquids and solids involved. This is discussed in detail in the American Chemical Society Publication entitled "Contact Angle, Wettability, and Adhesion" edited by Robert F. Gould and copyrighted in 1964. A fiber or surface of a fiber is said to be wetted by a liquid either when the contact angle between the liquid and the fiber or surface is less than 90__ or when the liquid will tend to spread spontaneously across the surface of the fiber; both conditions normally coexisting.

The fiber material can be added to the macrostructures by introducing the fibers into the treatment solution with the crosslinking, by mixing with the precursor particles prior to applying the treatment solution, or by adding the fiber material to the treatment solution/precursor particle mixture. For example, the fiber material can be kneaded into the treatment solution/precursor particle mixture. The fiber material is preferably thoroughly mixed with the solution so that the fiber material is uniformly dispersed throughout the macrostructure. The fibers are also preferably added before reacting the adduct with the polymer material of the precursor particles.

E. Optional Substrate Layer

If desired, the porous absorbent macrostructure can be attached to an optional substrate. See copending U.S. application Ser. No. 142,253 (Hsueh et al), filed Oct. 22, 1993, which is incorporated by reference. The substrate can provide a variety of functions, including: (1) improving the distribution of fluids to be absorbed by the macrostructure;

and (2) supporting the macrostructure by providing additional integrity, especially in the situation, where the absorbent particles begin to swell after absorbing fluid. The substrate can be made from various materials known in the art such as cellulose fibers, nonwoven webs, tissue webs, foams, polyacrylate fibers, apertured polymeric webs, synthetic fibers, metallic foils, elastomers, and the like. Most such substrate materials can distribute fluids to, as well as support the macrostructure. Preferably, the substrate is comprised of cellulosic material or a material having cellulosic functionality. Preferred substrates for distributing fluids are cellulosic materials, fibrous webs, cellulosic fibrous webs, solid foams, cellulosic foams, and polyvinyl alcohol foams. Preferred substrates for supporting the macrostructure are cellulosic materials, fibrous webs, nonwoven webs, fabrics, cellulosic fibrous webs, solid foams, cellulosic foams, and polyvinyl alcohol foams.

The substrate is preferably flexible and pliable to encourage such properties in the resulting absorbent composite with the macrostructure. The substrate can be substantially resilient and non-stretchable, or it can be stretchable or deformable to a varying extent in response to forces exerted normal to and in the plane of the surface of the substrate. The thickness and basis weight (weight per unit area of substrate) of the substrate material can vary depending on the type of substrate and properties desired. The substrate can comprise a plurality of individual sheets, or plies, of a particular substrate material, or a combination of one or more substrate layers in a laminate. One such suitable substrate is a Bounty® (registered trademark of Procter & Gamble Co.) sheet having a thickness of from about 0.02 mm to about 1.2 mm, more preferably from about 0.3 mm to about 0.8 mm, and a basis weight of from about 5 gm/m$^2$ to about 100 gm/m$^2$, more preferably from about 10 gm/m$^2$ to about 60 gm/m$^2$, and most preferably from about 15 gm/m$^2$ to about 40 gm/m$^2$. Another suitable substrate is a cellulose foam having a dry compressed thickness of from about 0.5 mm to about 3.0 mm, more preferably from about 0.8 mm to about 2.0 mm, a wet expanded thickness of from about 0.8 mm to about 6.0 mm, more preferably from about 1.0 mm to about 5.0 mm, and a basis weight of from about 50 gm/m$^2$ to about 2,000 gm/m$^2$, more preferably from about 100 gm/m$^2$ to about 1,000 gm/m$^2$.

Substrates suitable for supporting the macrostructure typically have a dry tensile strength of from about 500 gm/in to about 8,000 gm/in, more preferably from about 1,000 gm/in to about 3,000 gm/in, a wet tensile strength of from about 200 gm/in to about 5,000 gm/in, though more preferably from about 400 gm/in to about 1,000 gm/in, and a wet burst strength of from about 100 gm to about 2,000 gm, though more preferably from about 200 gm to about 1,000 gm. Preferred substrates of this type include cellulosic fibrous webs such as paper towels and tissues such those disclosed in U.S. Pat. No. 3,953,638, issued Apr. 27, 1976, U.S. Pat. No. 4,469,735, issued Sep. 4, 1984, U.S. Pat. No. 4,468,428, issued Aug. 28, 1984, and U.S. Pat. No. 4,986,882, issued Jan. 22, 1991, all of which are incorporated by reference. Another preferred substrate layer of this type is a cellulosic foam since it provides a higher fluid wicking rate over a longer wicking distance than a cellulosic fibrous web. Preferably, the cellulosic foam is in a compressed state so as to further improve its fluid wicking and distribution properties. Suitable cellulose foams can be made of regenerated rayon fibers by well-known methods, such as those disclosed in European patent application 293,208 (Uchida et al), published Nov. 30, 1988. incorporated herein by reference.

The porous absorbent macrostructure can be attached to the substrate by a variety of chemical, physical, and adhesive agents. Adhesive agents for attaching the substrate to the macrostructure include glues and hot melt adhesives. Preferably, the bonding between the substrate and macrostructure is achieved by depositing the precursor absorbent particles on the substrate, treating the deposited particles with the solution comprising a crosslinking agent and then curing the treated particles/substrate as previously. In a preferred embodiment of this method, a cellulosic substrate (e.g., paper towel) is used. The precursor absorbent particles are then deposited on this cellulosic substrate. A treatment solution comprising an amino-epichlorohydrin adduct, preferably polymeric epichlorohydrin-polyamide/polyamine wet strength resin such Kymene®, is then applied (e.g., sprayed) on the cellulosic substrate and the absorbent. The treated substrate/particles are then cured at ambient temperatures such that a porous macro structure is formed that is bonded to the cellulosic substrate.

II. Treating Macrostructure With Latex to Improve Flexibility

A. In General

The key aspect of the present invention is treating the above porous absorbent macrostructures (with or without the optional substrate) with certain latexes. As used herein, the term "latex" refers to an aqueous dispersion or emulsion of polymer particles in an aqueous phase, and can also be referred to as an emulsion polymer. As used herein, the term "sinter" refers to the fusion mechanism which occurs upon the drying of a suspended liquid emulsion or dispersion such as a latex; the use of "sinter" is synonmous with the phrase "film forming." Treatment of these macrostructures with these latexes has been found to dramatically increase the flexibility of the macrostructure, especially when in the form of a sheet and even when attached to a substrate such as a paper towel. In addition to improved flexibility, latex treatment according to the present invention improves the bonding between particles of the aggregates that comprise these macrostructures. This leads to improvements in the dry and wet integrity of the macrostructure. The presence of the latex also allows these macrostructures to be thermally bonded to nonwovens, such as the backsheet of an absorbent article (e.g., a diaper).

This latex treatment has also been found to enhance aging stability of these macrostructures, i.e., the ability to remain flexible when exposed to ambient and especially elevated temperatures (e.g., 50_C.) that can occur during storage and transportation of absorbent articles in which these macrostructures are typically used as absorbent members. For example, macrostructures in sheet form that have been treated with latex according to the present invention that been exposed to temperatures as high as 40_C. have maintained their desired flexibility for more than a month. In addition, latex treated macrostructures according to the present invention have been found to remain flexible at low relative humidities that can be encountered during winter months. For example, macrostructures in sheet form that have been treated with latex according to the present invention that have been exposed to relative humidities as low as 20% at room temperatures (23°–27° C.) have also maintained their desired flexibility for more than a month. By contrast, macrostructures in sheet form that have not treated with latex according to the present invention have been found to become more rigid or stiff when exposed to these higher temperatures and low relatively humidities. The improved flexibility of the macrostructures according to the invention after being subjected to such conditions is exhibited by the surprisingly improved bending modulus over macrostructures which have not been treated with latex (Example 3). Preferably, the bending modulus of the macrostructures is from about 0.1 to 1.0 gfcm²/cm and most preferably from about 0.1 to about 0.5 gfcm²/cm, as measured according to the test method described in Example 3 and based on a macrostructures having a basis weight (particles per layer) of from about 0.05 to about 0.8 g/in², preferably of about 0.2 g/in².

B. Latex Properties and Composition

It has been found that latexes suitable for use in the present invention need to have certain properties. One key property of these latexes is that they be "rubbery" at ambient temperatures or below after they have been sintered. In other words, latexes useful in the present invention have a glass transition temperature (Tg) of about 25_ or less. Preferably, these latexes have a Tg of about 10_C. or lower and, most preferably of about –10_C. or lower.

The ability of the latex to be "rubbery" at ambient temperatures after sintering is important to improving the flexibility of the macrostructure. It is believed that when the macrostructure is treated with the latex, the latex forms a coating on a portion, and typically a substantial portion of the particles. It should be understood that the latex coating can be continuous, but there is no such requirement as discontinuous latex coatings have been found to work, as well. The latex provides an elastomeric "shell" for the otherwise rigid, stiff, hard absorbent particle. As a result, the coated particles have a certain degree of malleability or springiness that allows the macrostructure, especially in sheet form to bend and flex.

Another important property of these latexes is the temperature at which they are capable of being sintered. Latexes useful in the present invention need to be sinterable at ambient temperatures or below. In other words, it is preferable for these latexes to be sinterable at a temperature of about $25_{13}$ C. or lower.

The ability of the latex to be sinterable at ambient temperatures is important in avoiding drying out the macrostructure. As noted above, the macrostructures used in the present invention are typically treated with a solution that comprises a relatively high level of water. This water is important in plasticizing the macrostructure to provide a certain degree of flexibility. If the latex used to treat this macrostructure requires a temperature much higher than ambient temperature (e.g., above 40_C.), this water is more likely to be driven off or evaporated, thus depriving the macrostructure of a certain degree of flexibility.

Another important property of these latexes is their hydrophilicity. To be useful in the present invention, the latex, when sintered needs to be at least somewhat hydrophilic. As used herein, the term "hydrophilic" describes a material, or surface of a material, that is wettable by aqueous fluids (e.g., aqueous body fluids) deposited on these materials. Hydrophilicity and wettability are typically defined in terms of contact angle and the surface tension of the fluids and solids involved. This is discussed in detail in the American Chemical Society publication entitled *Contact Angle, Wettability and Adhesion,* edited by Robert F. Gould (Copyright 1964). A material, or surface of a material, is said to be wetted by a fluid (i.e., hydrophilic) when either the contact angle between the fluid and the material, or its surface, is less than 90°, or when the fluid tends to spread spontaneously across the surface of the material, both conditions normally co-existing. Conversely, a material or surface is considered to be hydrophobic if the contact angle is greater than 900 and the fluid does not spread spontaneously across the surface of the material.

Hydrophilicity is desirable in insuring that the latex does not substantially affect fluid handling properties of the macrostructure. As noted above, it is believed that the latex coats a portion of the particles which means at least one, if not most, of the absorbent particles that comprise the macrostructure. If the latex, when sintered, is essentially hydrophobic, it could substantially affect the fluid handling properties of the macrostructure, especially by inhibiting the absorption of fluid by the particles that comprise the macrostructure. Latexes that are particularly preferred for use in the present invention are quite hydrophilic and thus do not interfere measurably with the fluid handling properties of the macrostructure.

Latexes useful in the present invention typically have powdery or fluid consistency. It is also desirable that the latex have a relatively high solids content. In this regard, suitable latexes will usually have a solids content of at least about 10% by weight and, more preferably at least about 45% by weight. Typically, latexes useful in the present invention will have a solids content of from about 45% to about 60% by weight of the latex.

Latexes useful in the present invention are typically prepared by emulsion polymerization of certain olefinic (ethylenically unsaturated) monomers. This emulsion polymerization can be carried out by customary methods using any of a variety anionic, nonionic, cationic, zwitterionic and/or amphoteric emulisifiers to stablize the resultant latex, including alkyl sulfates, alkylarylalkoxy sulfates, alkylarylsulfonates and alkali metal and/or ammonium salts of alkyl- and alkylaryl-polyglycol ether-sulfates; oxyethylated fatty alcohols or oxyethylated alkylphenols, as well as block copolymers of ethylene oxide and propylene oxide; cationic adducts of primary, secondary or tertiary fatty amines or fatty amine oxyethylates with organic or inorganic acids, and quaternary alkylammonium surfactants; and alkylamidopropylbetaines. The olefinic monomer can be a single type of monomer or can be mixture of different olefinic monomers, i. e. to form copolymer particles dispersed or emulsified in the aqueous phase. The latex suitable for use herein is preferably neutral or has no ionic charge, vis-a-vis, the latex is not cationic or anionic in nature.

Suitable latexes can be prepared via emulsion polymerization from olefinic monomers that include the $C_2$–$C_4$ alkyl and hydroxy alkyl acrylates, such as those selected from the group of propyl acrylate, n-butyl acrylate, isobutyl acrylate, 2-hydroxyethyl acrylate, 2-hydroxypropyl acrylate, ethyl acrylate and mixtures thereof. Also suitable are $C_1$–$C_4$ alkyl or hydroxy alkyl methacrylates selected from the group of propyl methacrylate, n-butyl methacrylate, isobutyl methacrylate, 2-hydroxyethyl methacrylate, 2-hydroxypropyl methacrylate, ethyl methacrylate, methyl methacrylate, vinyl acetate and mixtures thereof. Also suitable are mixtures of the aforementioned $C_2$–$C_4$ alkyl and hydroxy alkyl acrylates and $C_1$–$C_4$ alkyl or hydroxy alkyl methacrylates. Especially suitable for use in the invention is an emulsion of polymethyl methacrylate. Particularly preferred latexes include those sold under the tradename MONWINYL 963 by Hoechst Celanese and RHOPLEX E1845 by Rohm & Haas.

Latexes suitable for use in the present invention can also be prepared by core-shell methods such as are disclosed in U.S. Pat. No. 4,419,471 (Nelsen et al), issued Dec. 6, 1983 and U.S. Pat. No. 4,734,445 (Noda et al), Mar. 29, 1988.

Core-shell methods generally involve providing an emulsion comprising discrete particles of "rubbery," elastomeric polymer, typically a styrene-butadiene copolymer, in an aqueous vehicle. An olefinic monomer, or monomer mixture, as described above is then intimately mixed with this emulsion containing the dispersed, "rubbery" polymer particles. This mixture is then reacted under conditions effective to polymerize the olefinic monomer(s) to form discrete composite particles comprising cores of the "rubbery" polymer that are at least partially encased by an integral shell of the polymer formed from the olefinic monomer(s).

C. Methods for Treating Macrostructures with Latex

In preparing the porous absorbent macrostructures of the present invention having improved flexibility, the macrostructure is treated with an effective amount of these latexes to coat at least some of the absorbent particles. What constitutes a "effective amount" will depend on a variety of factors, including the particular porous absorbent macrostructure involved, the particular latex used, the flexibility benefits desired, and like factors. Most preferably, treating the macrostructure with about 2% by weight latex will be sufficient to impart noticeable improvements in the flexibility of the macrostructure. However, the macrostructure can be effectively treated with from about 1% to about 10% by weight, and more preferably from about 2% to about 5% by weight of latex.

The porous absorbent macrostructure can be treated with the latex by any of the variety of methods suitable for applying additives to conventional substrates. Suitable methods includes spraying, printing (e.g., flexographic printing), coating, e.g., gravure coating, dipping, brushing, foaming or combinations of such application techniques. Typically, the latex is sprayed onto the already formed porous absorbent macrostructure and then sintered at ambient temperature, e.g., at about 25_C. or lower. Additionally, latex treatment can assist in the forming of a more stable macrostructure by providing improved particle immobilization.

Besides spraying on the latex on the already formed, macrostructure, other methods can also be used to treat the porous absorbent macrostructure with the latex. One such method involves blending the latex with the untreated precursor absorbent particles and then treating this latex/particle blend with the solution containing the crosslinking agent plus any other optional components such as glycerol. This treated latex/particle blend can then be cured at ambient temperature, e.g., at about $25_{13}$ C. or lower, to provide porous absorbent macrostructure having improved flexibility.

Another method involves casting the latex as a thin film. The precursor absorbent particle can then be deposited onto this cast film. The cast film with the deposited particles is then treated (such as by spraying) solution containing crosslinking agent and any other optional components. This treated particle/latex film can then be cured at ambient temperature, e.g., at about $25_{13}$ C. or lower, to provide porous absorbent macrostructure having improved flexibility. In addition, the sintered latex film can function as a supporting substrate for the macrostructure to provide dry and especially wet integrity.

Yet another method involves pressurizing latex in a container such that it can be blown or sprayed onto the precursor particles in the form of a foam, after which a compression roll or the like is used to spread the latex evenly. The blown or sprayed foam latex is to some extent in the form of porous fibers which are extremely porous and further enhance the absorbency of the macrostructure. A latex treated macrostructure of this type in which the precursor particles swell into the porous latex fibers has improved structural integrity.

IV. USES OF THE MACROSTRUCTURES

The porous, absorbent macrostructures can be used for many purposes in many fields of use. For example, the macrostructures can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials.

Because of the unique absorbent properties of the porous, absorbent macrostructures of the present invention, they are especially suitable for use as absorbent cores in absorbent articles, especially disposable absorbent articles. As used herein, the term "absorbent article" refers to articles which absorb and contain body exudates and more specifically refers to articles which are placed against or in proximity to the body of the wearer to absorb and contain the various exudates discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). A preferred embodiment of a disposable absorbent article, diaper 20, is shown in FIG. 3. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like.

FIG. 3 is a perspective view of the diaper 20 of the present invention in its uncontracted state (i.e., with all the elastic induced contraction removed) with portions of the structure being cut-away to more clearly show the construction of the diaper 20 and with the portion of the diaper 20 which contacts the wearer facing the viewer. The diaper 20 is shown in FIG. 3 to preferably comprise a liquid pervious topsheet 38; a liquid impervious backsheet 40 joined with the topsheet 38; an absorbent core 42 positioned between the topsheet 38 and the backsheet 40; elastic members 44; and tape tab fasteners 46. While the topsheet 38, the backsheet 40, the absorbent core 42, and the elastic members 44 can be assembled in a variety of well known configurations, a preferred diaper configuration is described generally in U.S. Pat. No. 3,860,003 (Buell), issued Jan. 14, 1975, which is incorporated by reference. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; and U.S. Pat. No. 4,816,025 (Foreman), issued Mar. 28, 1989, all of which are incorporated by reference.

FIG. 3 shows a preferred embodiment of the diaper 20 in which the topsheet 38 and the backsheet 40 are co-extensive and have length and width dimensions generally larger than those of the absorbent core 42. The topsheet 38 is joined with and superimposed on the backsheet 40 thereby forming the periphery of the diaper 20. The periphery defines the outer perimeter or the edges of the diaper 20. The periphery comprises the end edges 32 and the longitudinal edges 30.

The topsheet 38 is compliant, soft feeling, and non-irritating to the wearer's skin. Further, the topsheet 38 is liquid pervious permitting liquids to readily penetrate through its thickness. A suitable topsheet 38 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent core 42.

A particularly preferred topsheet 38 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 38. For example, the topsheet 38 can be woven, nonwoven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction, and a wet tensile strength of at least about 55 grams per centimeter in the cross-machine direction.

The backsheet 40 is impervious to liquids and is preferably manufactured from a thin plastic film, although other flexible liquid impervious materials may also be used. The s backsheet 40 prevents the exudates absorbed and contained in the absorbent core 42 from wetting articles which contact the diaper 20 such as bed sheets and undergarments.

Preferably, the backsheet 40 is polyethylene film having a thickness from about 0.012 mm (0.5 mil) to about 0.051 centimeters (2.0 mils), although other flexible, liquid impervious materials can be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more cloth like appearance. Further, the backsheet 40 may permit vapors to escape from the absorbent core 42 while still preventing exudates from passing through the backsheet 40.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 centimeters to about 2.5 centimeters (about 0.5 to about 1.0 inch) around the entire diaper periphery.

The topsheet 38 and the backsheet 40 are joined together in any suitable manner. As used herein, the term "joined" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment the topsheet 38 and the backsheet 40 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 38 to the backsheet 40.

Tape tab fasteners 46 are typically applied to the back waistband region of the diaper 20 to provide a fastening means for holding the diaper on the wearer. The tape tab fasteners 46 can be any of those well known in the art, such as the fastening tape disclosed in U.S. Pat. No. 3,848,594 (Buell), issued Nov. 19, 1974, which is incorporated by reference. These tape tab fasteners 46 or other diaper fastening means are typically applied near the corners of the diaper 20.

The elastic members 44 are disposed adjacent the periphery of the diaper 20, preferably along each longitudinal edge 30, so that the elastic members 44 tend to draw and hold the diaper 20 against the legs of the wearer. Alternatively, the elastic members 44 can be disposed adjacent either or both of the end edges 32 of the diaper 20 to provide a waistband as well as or rather than leg cuffs. For example, a suitable waistband is disclosed in U.S. Pat. No. 4,515,595 (Kievit et al), issued May 7, 1985, which is incorporated by reference. In addition, a method and apparatus suitable for manufacturing a disposable diaper having elastically contractible elastic members is described in U.S. Pat. No. 4,081,301 (Buell), issued Mar. 28, 1978, which is incorporated by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 can be stretched and secured while the diaper 20 is in an uncontracted condition. Alternatively, the diaper 20 can be contracted, for example, by pleating, and the elastic members 44 secured and connected to the diaper 20 while the elastic members 44 are in their unrelaxed or unstretched condition.

In the embodiment illustrated in FIG. 3, the elastic members 44 extend along a portion of the length of the diaper 20. Alternatively, the elastic members 44 can extend the entire length of the diaper 20, or any other length suitable to provide an elastically contractible line. The length of the elastic members 44 is dictated by the diaper design.

The elastic members 44 can be in a multitude of configurations. For example, the width of the elastic members 44 can be varied from about 0.25 millimeters (0.01 inches) to about 25 millimeters (1.0 inch) or more; the elastic members 44 can comprise a single strand of elastic material or can comprise several parallel or non-parallel strands of elastic material; or the elastic members 44 can be rectangular or curvilinear. Still further, the elastic members 44 can be affixed to the diaper in any of several ways which are known in the art. For example, the elastic members 44 can be ultrasonically bonded, heat and pressure sealed into the diaper 20 using a variety of bonding patterns or the elastic members 44 can simply be glued to the diaper 20.

The absorbent core 42 of the diaper 20 is positioned between the topsheet 38 and the backsheet 40. The absorbent core 42 can be manufactured in a wide variety of sizes and shapes (e.g., rectangular, hourglass, asymmetrical, etc.) and from a wide variety of materials. The total absorbent capacity of the absorbent core 42 should, however, be compatible with the design liquid loading for the intended use of the absorbent article or diaper. Further, the size and absorbent capacity of the absorbent core 42 can vary to accommodate wearers ranging from infants through adults. The absorbent core 42 comprises the porous, absorbent macrostructures of the present invention.

A preferred embodiment of the diaper 20 has a rectangular-shaped absorbent core 42. As shown in FIG. 4, the absorbent core 42 preferably comprises an absorbent member 48 comprising an envelope web 50 and a porous, absorbent macrostructure 52 disposed in the envelope web 50. The macrostructure 52 is encased in the envelope web 50 to minimize the potential for the precursor particles to migrate through the topsheet and to provide an additional liquid transport layer between the topsheet 38 and the macrostructure 52 to enhance liquid acquisition and minimize rewet. As shown in FIG. 4, a single envelope web 50 is wrapped about the macrostructure 52 by folding to form a first layer 54 and a second layer 56. The edges 58 of the envelope web 50 are sealed about its periphery by any conventional means such as an adhesive 59 (as shown), ultrasonic bonds, or heat/pressure bonds, to form a pouch. The envelope web 50 can comprise a number of materials including nonwoven webs, paper webs, or webs of absorbent materials such as tissue paper. The envelope web 50 preferably comprises a nonwoven web similar to the webs used to form the topsheet 38. The nonwoven web is preferably hydrophilic to allow liquids to rapidly pass through the envelope web 50. Similar layered absorbent members (laminates) are more fully described in U.S. Pat. No. 4,578,068 (Kramer et al), issued Mar. 25, 1986, which is incorporated by reference.

Alternatively, the absorbent cores 42 of the present invention can consist solely of one or more (a plurality of the) porous, absorbent macrostructures of the present invention; can comprise a combination of layers including the macrostructures of the present invention; or any other absorbent core configurations including one or more of the macrostructures of the present invention.

FIG. 5 shows an alternative embodiment of the diaper 120 comprising a dual-layer absorbent core 142 comprising a modified hourglass-shaped absorbent member 60 and a sheet 62 of the porous, absorbent macrostructure positioned subjacent the absorbent member 60 (i.e., between the absorbent member 60 and the backsheet 40).

The absorbent member 60 serves to quickly collect and temporarily hold discharged liquids and to transport such liquids by wicking from the point of initial contact to other parts of the absorbent member 60 and to the macrostructure sheet 62. The absorbent member 60 preferably comprises a web or batt of fiber materials. Various types of fiber material can be used in the absorbent member 60 such as the fiber materials previously discussed herein. Cellulosic fibers are generally preferred for use herein, wood pulp fibers being especially preferred. The absorbent member 60 can also contain specific amounts of a particulate, absorbent, polymeric composition. The absorbent member 60, for example, can contain up to about 50% by its weight of the polymeric composition. In the most preferred embodiments, the absorbent member 60 contains from 0% to about 8% by its weight of a particulate, absorbent, polymeric composition. In alternatively preferred embodiments, the absorbent member 60 comprises chemically stiffened cellulosic fibers as previously discussed herein. Exemplary embodiments of the absorbent member 60 useful in the present invention are described in U.S. Pat. No. 4,673,402 (Weisman et al), issued Jun. 16, 1987; and U.S. Pat. No. 4,834,735 (Alemany et al), issued May 30, 1989, both of which are incorporated by reference. Absorbent members having a storage zone and an acquisition zone having a lower average density and a lower average basis weight per unit area than the storage zone so that the acquisition zone can effectively and efficiently rapidly acquire discharged liquid are especially preferred for use herein.

The absorbent member 60 can be of any desired shape, for example, rectangular, oval, oblong, asymmetric or hourglass-shaped. The shape of the absorbent member 60 can define the general shape of the resulting diaper 120. In the preferred embodiments as shown in FIG. 5, the absorbent member 60 is hourglass-shaped.

The macrostructure sheet 62 of the present invention need not be the same size as the absorbent member 60 and can, in fact, have a top surface which is substantially smaller or larger than the top surface area of the absorbent member 60. As shown in FIG. 5, the macrostructure sheet 62 is smaller than the absorbent member 60 and has a top surface area from about 0.10 to about 1.0 times that of the absorbent member 60. Most preferably, the top surface area of the macrostructure sheet 62 will be only from about 0.10 to about 0.75, and most preferably from about 0.10 to about 0.5 times that of the absorbent member 60. In an alternative embodiment, the absorbent member 60 is smaller than the macrostructure sheet 62 and has a top surface area from about 0.25 to about 1.0 times, more preferably from about 0.3 to about 0.95 times that of the macrostructure sheet 62. In this alternative embodiment, the absorbent member 60 preferably comprises chemically stiffened cellulosic fibers, as previously described.

The macrostructure sheet 62 is preferably placed in a specific positional relationship with respect to the backsheet 40 and/or the absorbent member 60 in the diaper. More particularly, the macrostructure sheet 62 is positioned generally toward the front of the diaper so that the macrostructure sheet 62 is most effectively located to acquire and hold discharged liquids.

In alternatively preferred embodiments, a plurality of macrostructures, preferably from two to six macrostructure strips or sheets, can be substituted for the single macrostructure sheet 62 shown in FIG. 5. Further, additional absorbent layers, members, or structures can be placed into the absorbent core 142. For example, an additional absorbent member can be positioned between the macrostructure sheet 62 and the backsheet 40 to provide reserve capacity for the absorbent core 142 and/or a layer to distribute liquids passing through the macrostructure sheet 62 to other portions of the absorbent core 142 or to the macrostructure sheet 62. The macrostructure sheet 62 can also alternatively be positioned over the absorbent member 60 so as to be positioned between the topsheet 38 and the absorbent member 60.

Figure 6:
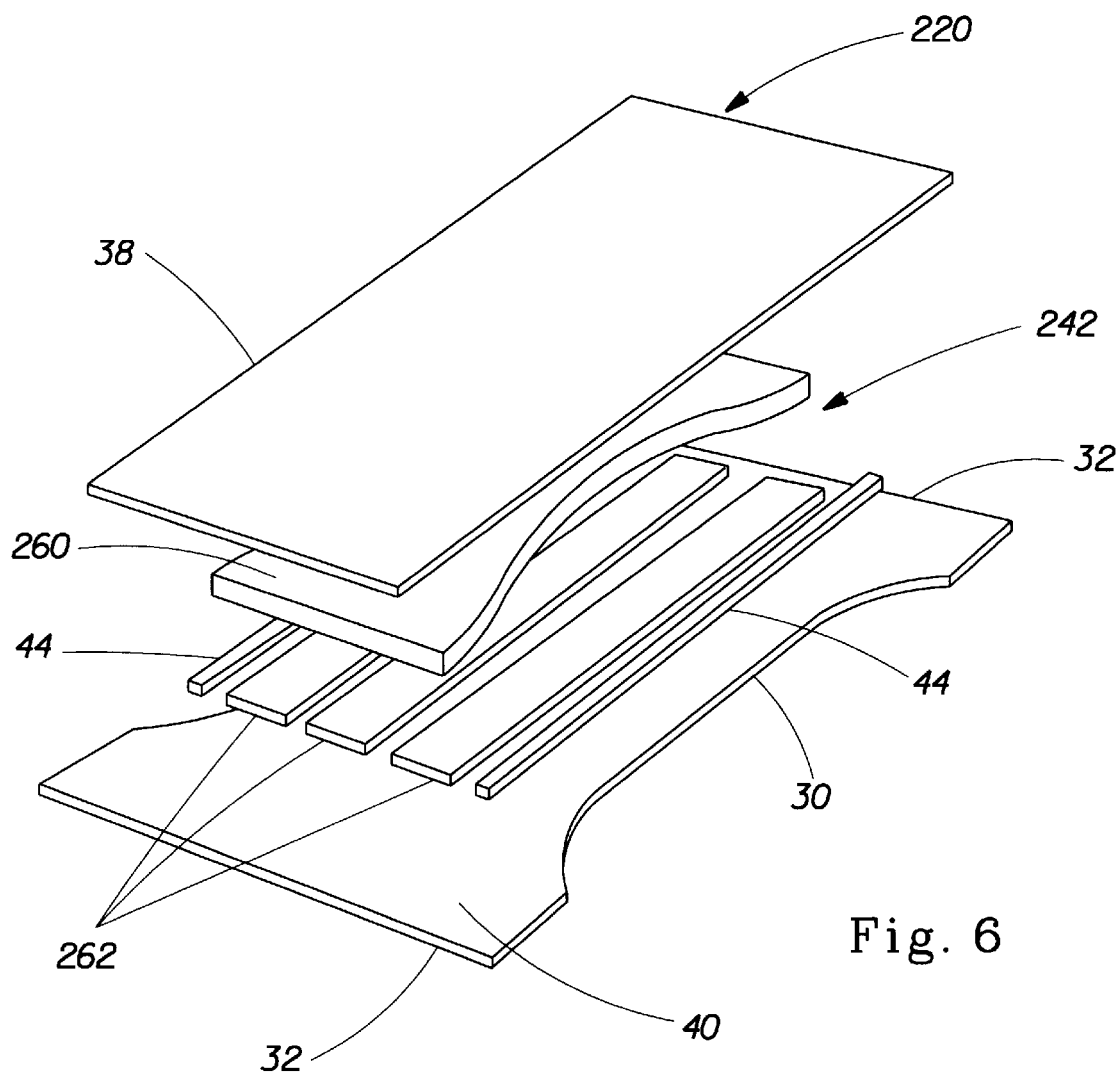
FIG. 6 is a blown-apart view of the components of a diaper structure, one of the components being an alternative dual-layer absorbent core where the absorbent nacrostructure is in the form of a plurality of strips.

FIG. 6 shows an alternative embodiment of a diaper 220 comprising an alternative dual-layer absorbent core 242 comprising a rectangular shaped absorbent member 260 and three elongated parallel spaced macrostructure strips 262 positioned between absorbent member 260 and backsheet 40.

The absorbent member 260 serves to quickly collect and temporarily hold discharged liquids and to tranport such liquids by wicking from the point of initial contact to other parts of the absorbent member 260 and to macrostructure strips 262. This absorbent member 260 preferably comprises a web or bat of fiber materials, most preferably chemically stiffened cellulosic fibers as previously discussed herein. Macrostructure strips 262 together act to acquire and hold the discharged liquids. By spacing macrostructure strips 262 from one another, a more effective surface area is presented for acquiring and holding the discharge liquids. This is particularly true since the spaced macrostructure strips 262 can swell and expand in the direction of their width, without interfering with the ability of adjacent strips to acquire discharged liquids.

In use, the diaper 20 is applied to a wearer by positioning the back waistband region under the wearer's back and drawing the reminder of the diaper 20 between the wearer's legs so that the front waistband region is positioned across the front of the wearer. The tape-tab fasteners 46 are then secured preferably to outwardly facing areas of the diaper 20. In use, disposable diapers or other absorbent articles incorporating the porous, absorbent macrostructures of the present invention tend to more quickly and efficiently distribute and store liquids and to remain dry due to the high absorbent capacity of the macrostructures. Disposable diapers incorporating the macrostructures of the present invention can also be thinner and more flexible.

V. PRECURSOR PARTICLE EXAMPLE

A jacketed 10 liter twin arm stainless steel kneader measuring 220 mm×240 mm in the opening and 240 mm in depth, and having two Sigma type blades possessing a rotational diameter of 120 mm is sealed with a lid. An aqueous monomer solution is prepared consisting of 37 weight % of monomer and 1.7 grams of trimethylol propane triacrylate. The monomer consists of 75 mole % sodium acrylate and 25 mole % acrylic acid. 5500 grams of the aqueous monomer solution is charged to the kneader vessel, which is subsequently purged with nitrogen gas to remove the remaining entrapped air. Then, the two Sigma type blades are set rotating at rates of 46 rpm and the jacket is heated by the passage of 35° C. water. 2.8 g of sodium persulfate and 0.14 g of L-ascorbic acid are added as polymerization initiators. Polymerization begins about four minutes after the addition of the initiators. A peak temperature of 82° C. is reached inside the reaction system 15 minutes after the addition of the initiators. The hydrated gel polymer is divided into particles about 5 mm in size as the stirring is continued. The lid is removed from the kneader 60 minutes after the start of the polymerization and the material is removed from the kneader.

The resultant hydrated aqueous gel polymer thus obtained is spread on a standard #50 size metal gauze and dried with hot air at 150° C. for 90 minutes. The dried particles are pulverized with roller mills and sifted with a standard #20 sieve (850 microns) to obtain particles that pass through the standard #20 sieve. A liquid mixture containing 0.5 parts of glycerol, 2 parts of water, and 0.5 parts of isopropanol is mixed with 100 parts of the particles. The resulting mixture of liquid and particles is charged into a bowl which is then dipped in a hot oil bath (195_C.) for 45 minutes in order to heat the mixture. The mixture is stirred while being heated. The mass average particle size of the final particles is 450 microns.

VI. SPECIFIC ILLUSTRATIONS OF PREPARATION OF MACROSTRUCTURES ACCORDING TO PRESENT INVENTION

Example 1

In this example, 80 parts of precursor particles made in accordance with the precursor particle example and having the particle size characteristics described in Example 1 are used. An aqueous treatment solution prepared from a mixture of 6.0 parts Kymene® Plus (30% resin active commercially available from Hercules Inc.), 3.5 parts water and 8.5 parts glycerol is also used.

A reciprocating table or shuttle is used in conjunction with a pair of sprayers that apply the treatment solution and a vibratory feeder that deposits the precursor particles. The sprayers and feeder are positioned above the reciprocating surface of the table. Initially a substrate material consisting of a double-ply Bounty® (trademark of Procter & Gamble) type sheet is placed onto the surface of the table. Then, the table with the Bounty® Sheet moves underneath the sprayers, the treatment solution is sprayed onto the surface of the Bounty® Sheet (or layer of particles) in a predetermined pattern. As the surface of the table moves further in the same direction and underneath the feeder, a predetermined amount of precursor particles are deposited onto the Bounty® Sheet surface (or previous layer of treated particles in subsequent passes). Optionally, after the particles have been deposited from the feeder to form a layer thereof, the surface of the table can move back in the opposite direction so that the sequence of applying treatment solution/depositing a layer of particles can be repeated.

A single layer of precursor particles (0.2 g/in$^2$ of particles per layer) is deposited from the feeder. After the layer of precursor particles has been deposited, a predetermined amount of the treatment solution is sprayed on top of each layer. The amount of treatment solution sprayed initially onto the surface of the table, as well as the layer of precursor particles, is about 0.010 g/in$^2$.

After the layering of precursor particles and spraying with treatment solution is complete, a relatively cohesive composite sheet of particles is formed. The cohesive composite sheet is then passed under a standard Preval sprayer which sprays a latex (Mowinyl 963, Hoechst Celanese) composition onto the sheet in an amount sufficient to have the final sheet composition contain about 2% by weight of the latex. This cohesive composite sheet is then fed by a belt to a compaction unit. The compaction unit consists of two coated steel compaction rolls (nip rolls) with a fixed (but variable) gap. The compaction rolls have a diameter of about 8 inches (20 cm) and are driven at a rate of about 20 rpm. The gap between the compaction rolls is about 0.05 inches (1.25 mm). The resultant aggregate composite sheets (density of $0.9 \geq 1.0$ g/cc) are stored in plastic bags at ambient room temperature (about 65° C.–72° C., 18.3° C.–22.2° C.) for about 24 hours. During this ambient temperature curing, the Kymene® Plus reacts with the polymer material in the surface of the precursor particles, thus causing effective crosslinking. The Kymene® Plus in the treatment solution also bonds to the cellulose structure of the Bounty® Sheet and to the precursor particles, to cause the Bounty® Sheet and the cohesive layers of particles to bond together. The ambient temperature cured sheets have a thickness (caliper) of about 0.06–0.07 inches (1.5–1.8 mm) and a width of about 4 inches (10 cm). These ambient temperature cured composite sheets have excellent flexibility and tensile strength, and can be handled easily without breaking or tearing.

Example 2

Figure 7:
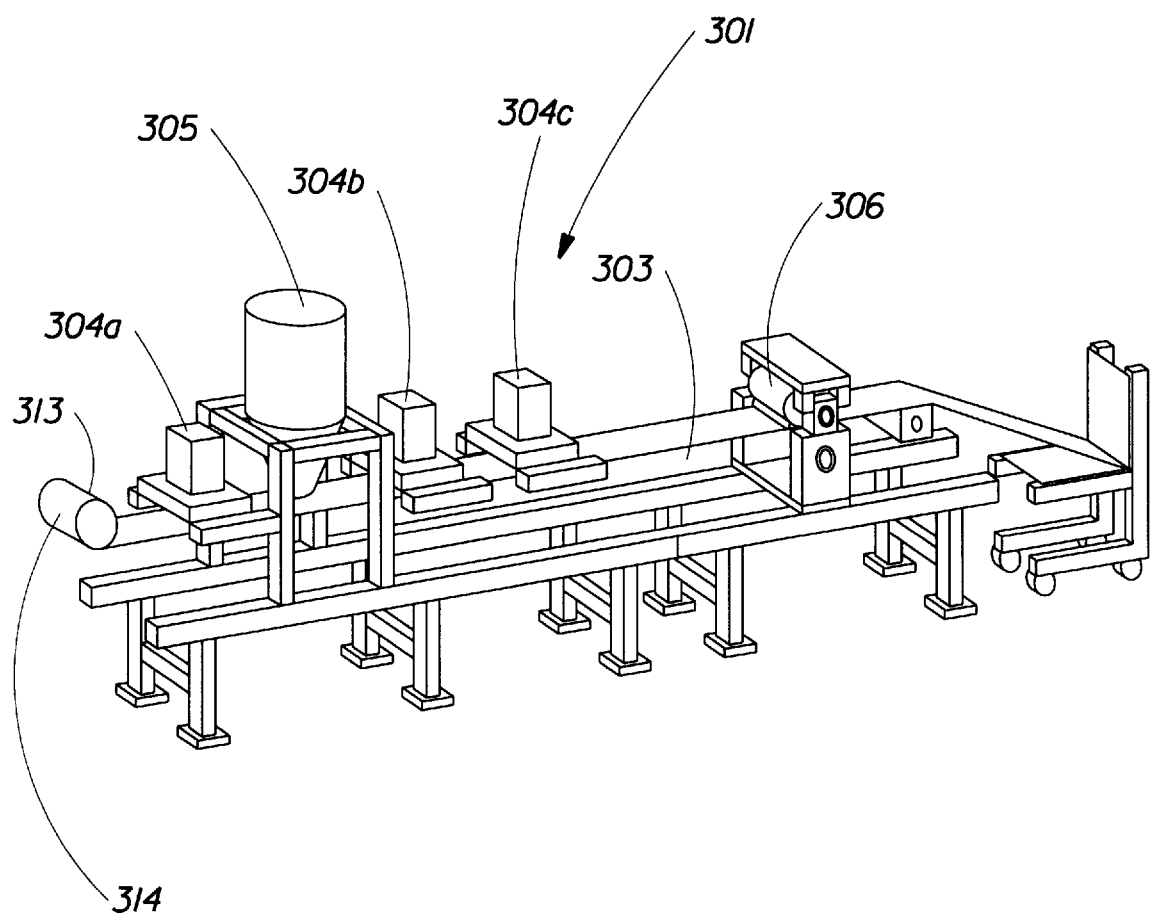
FIG. 7 is a simplified perspective view of an apparatus for making absorbent macrostructures of the present invention in the form of sheets.

In this example, apparatus 301 shown in FIG. 7 is used. The precursor particles used are made in accordance with the precursor particle example and have a size between 150–550 microns. An aqueous treatment solution is prepared from a mixture of 5.0 parts Kymene® Plus (30% resin active), 7.1 parts of water and 12.7 parts glycerol. Feeder 305 is a Super Feeder model # 210 SE-00354 vibrating feeder, available from Solids Flow Control, of Charlotte, N.C. Sprayers 304 are model 6218-1/4 JAU atomized air actuated nozzle assemblies, available from Spraying Systems, Co., of Wheaton, Ill. For the first two applications, sprayers 304a and 304b deliver the treatment solution to conveyor 303 at a rate of 39.8 grams/min. Sprayer 304c delivers the latex composition to conveyor 303. Conveyor 303 is a moving conveyor made from polyurethane, and travels at a speed of 27 ft./min. Sheet feeder 313 includes a rolled substrate sheet consisting of a double-ply Bounty® type sheet 314 to supply the Bounty® sheet to conveyor 303 synchronized with the rate of conveyor 303. The pressure applicators are a pair of compaction rolls 306 having 8 inch (20 cm) diameters and being 12 inches (30.5 cm) wide. The top and bottom rolls 306 are coated with a # 934 Plasma Coating, available from Plasma Coatings, Inc., of Waterbury, Conn.

This example is carried out according to the following steps:

STEP 1: Supply the Bounty® sheet 314 to conveyor 303 in synchronization with the rate of conveyor 303.

STEP 2: Spray a predetermined area of the surface of supplied Bounty sheet with treatment solution in an amount substantially equal to 0.05 grams of solution per square inch of the Bounty® sheet.

STEP 3: Layer substantially continuously 0.2 grams of precursor particles per square inch of the Bounty® sheet onto the same predetermined area.

STEP 4: The first layer of precursor particles on the predetermined area of the Bounty® sheet is sprayed with treatment solution in an amount substantially equal to 0.05 grams of solution per square inch of Bounty® sheet.

STEP 5: The absorbent composite is sprayed using sprayer 304c with 0.01 grams of a latex composition (Mowinyl 963, Hoechst Celanese).

STEP 6: The absorbent composite is passed through the compaction rolls 306. The gap between the compaction rolls 306 is 0.03 inches. This produces a sheet having a density of 0.70 g/cc.

STEP 7: The sheet is cured and the latex is sintered to the outer most layer of the sheet by placing it in a plastic bag and allowing it to sit at ambient temperature (72° F., 22.2° C.) for 48 hours.

The resultant absorbent composite sheet has good flexibility, dry integrity properties, and free gel blocking.

Example 3

An absorbent composite sheet made according to Example 2 is cut into two 1 cm×10 cm sample sheets which are tested as follows for flexibility indicated by the bending modulus (gfcm$^2$/cm or gram force cm$^2$/cm) of the sheets. Another absorbent composite sheet is made according to Example 2 except that it is not treated with latex. Two 1 cm×10 cm sample sheets are cut from the non-latex treated composite sheet. Flexible sample sheets give low bending modules values while rigid sample sheets have high bending modulus values. One latex-treated sample sheet and one non-latex treated sample sheet are exposed to a 50° C. environment for 48 hrs, after which the bending modules is measured for each sample sheet. Each sample sheet is placed into the sample holder of the bending tester. The bending tester used is commercially available from Kato Tech. Co. LTD. (Nihonseimei Kyoto Santetsu Bldg. 3F 608-9 Higashishikoji-cho Shiokoji Agaru Nisginotoindohri Shimogyo-ku, Kyoto, Japan) under the tradename Pure Kawabata Bending tester. Each sample sheet is bent 150° clockwise, and then 300° counterclockwise. The force for bending the sample sheet is recorded and converted to gfcm$^2$/cm units. The latex-treated sample sheets have bending modulus values of 0.17 gfcm$^2$/cm and 0.36 gfcm$^2$/cm (aged in 50_C. for 48 hrs.) while the non-latex treated sample sheets values of 0.32 gfcm$^2$/cm and _5.0 gfcm$^2$/cm (aged in 50_C. for 48 hrs.). As can be seen from these bending modulus values, the latex-treated sample sheets have surprisingly improved flexibility over the non-latex treated sample sheets which are very rigid and even crack after being exposing to elevated temperatures and low humidity.

Example 4

After preparing a cutting table, the continuous absorbent composite of Example 2 is placed on a flat cutting surface. A punch cutter which comprises 20 cylindrical blades faced to outside is prepared. Each of the blades has a diameter of 10 mm and the distance between centers of adjacent two blades is designed at 20 mm. The punch cutter is pushed down on the continuous absorbent composite. Therefore, applying adequate pressure (about 0.5–5 kgf/cm$^2$) through the punch cutter to the continuous absorbent composite on the flat cutting surface, 20 of circular voids penetrating the composite can be formed in the absorbent composite. As a result, a non-continuous absorbent composite can be obtained.

Example 5

After preparing a cutting table, a continuous absorbent sheet of Example 2 is placed on a flat cutting surface. A punch cutter which comprises 20 circular blades faced to outside is prepared. Each of the blades has a diameter of 10 mm and the distance between centers of adjacent two blades is designed at 20 mm. The punch cutter is pushed down on the continuous absorbent composite. Therefore, applying adequate pressure (about 0.5–5 kgf/cm$^2$) through the punch cutter to the continuous absorbent sheet on the flat cutting surface, 20 of circular voids penetrating the composite can be formed in the absorbent sheet. As a result, a non-continuous absorbent sheet can be formed.

A double-ply Bounty® sheet having the same size as the non-continuous absorbent sheet is prepared and the treatment solution is also sprayed onto the Bounty® sheet with the Preval sprayer. After the cellulosic material of the surface of the Bounty® sheet is treated with a sufficient amount (e.g. an amount substantially equal to 0.05 grams of solution per square inch) of the treatment solution uniformly, the non-continuous absorbent sheet is placed on the surface of the Bounty® sheet. The two sheets are extruded into the compaction rolls and are applied an opposing pressure thereby. As a result, a semi-continuous absorbent composite can be obtained.

What is claimed is:

1. A method for imparting improved flexibility to a porous, absorbent macrostructure, said method comprising the steps of:

(a) treating a porous aggregate macrostructure comprising an interparticle bonded aggregate having pores interconnected by intercommunicating channels such that the macrostructure is liquid permeable with an effective amount of a latex to coat a portion of said particles of said porous aggregate macrostructure, said latex being capable of being sintered at a temperature of about 25°

C. or lower, being at least somewhat hydrophilic when sintered, and having a Tg of about 25° C. or lower when sintered; and (b) sintering said porous aggregate macrostructure at a temperature of about 25° C. or lower to impart increased flexibility thereto.

2. The method of claim 1 wherein said porous aggregate macrostructure is in the form of a sheet having thickness of at least about 0.2 mm and a density of from about 0.5 to about 1.0 g/cc.

3. The method of claim 2 wherein said latex is made by emulsion polymerization of an olefinic monomer selected from the group consisting of $C_2$–$C_4$ alkyl and hydroxy alkyl acrylates, $C_1$–$C_4$ alkyl or hydroxy alkyl methacrylates and mixtures thereof.

4. The method of claim 3 wherein said $C_2$–$C_4$ alkyl and hydroxy alkyl acrylates are selected from the group consisting of propyl acrylate, n-butyl acrylate, isobutyl acrylate, 2-hydroxyethyl acrylate, 2-hydroxypropyl acrylate, ethyl acrylate and mixtures thereof.

5. The method of claim 3 wherein said $C_1$–$C_4$ alkyl or hydroxy alkyl methacrylates are selected from the group consisting of propyl methacrylate, n-butyl methacrylate, isobutyl methacrylate, 2-hydroxyethyl methacrylate, 2-hydroxypropyl methacrylate, ethyl methacrylate, methyl methacrylate, vinyl acetate and mixtures thereof.

* * * * *

UNITED STATES PATENT AND TRADEMARK OFFICE
CERTIFICATE OF CORRECTION

PATENT NO.    : 5,859,074
DATED         : January 12, 1999
INVENTOR(S)   : Rezai et al.

It is certified that error appears in the above-identified patent and that said Letters Patent is hereby corrected as shown below:

Title page,
Item [57], ABSTRACT,
Line 7, please delete "macrostructure" and insert therefor -- macrostructure --.

Column 2,
Line 12, please add the following paragraph
-- A more recent solution proposed to overcome the problem of absorbent particle mobility is to form these particles into aggregate macrostructures, typically as sheets of bonded absorbent particles. See, for example, U.S Patent 5,102,597 (Roe et al), issued April 7, 1992; U.S. Patent 5,124,188 (Roe et al), issued June 23, 1992; and U.S. Patent 5,149, 344 (Lahrman et al), issued September 22, 1992. These aggregate macrostructures are prepared by initially mixing the absorbent particles with a solution of a nonionic crosslinking agent such as glycerol, water and a hydrophilic organic solvent such as isopropanol. Particulate absorbent polymer compositions of the type used in making these aggregate macrostructures usually contain multiple carboxy groups and are typically derived from polycarboxy compounds such as the polyacrylates. When using glycerol as the crosslinking agent, the hydroxy groups of the glycerol typically react with the carboxy groups of the polymers present in the absorbent particles by an esterification reaction. The crosslinked, ester bond formed by glycerol occurs not only at the surface of the absorbent particles, but also inside particles. This is due to the fact that glycerol is a nonionic, relatively small molecule that can penetrate inside the absorbent particles. The resulting internal crosslinking leads to a lower absorbent capacity for the bonded particles of the aggregate macrostructures. --.
Line 48, please delete "50_C." and insert therefor -- 50°C. --.
Line 65, please delete "identifed" and insert therefor -- identified --.
Line 65, after "porous", please insert -- , -- (a comma).

Column 3,
Lines 14, 15, 34, 36 and 38, please delete "$25_{13}$C." and insert therefor -- 25°C. --.
Line 46, please delete "50_C." and insert therefor -- 50°C. --.

Column 4,
Lines 10-11, please delete "nacrostruc-ture" and insert therefor -- macrostructure --.

Column 7,
Lines 28, 43 and 49, please delete "precusor" and insert therefor -- precursor --.

Column 12,
Line 24, please delete "18°to" and insert therefor -- 18° to --.
Line 35, please delete "N-amninoethyl" and insert therefor -- N-aminoethyl --.

UNITED STATES PATENT AND TRADEMARK OFFICE
CERTIFICATE OF CORRECTION

PATENT NO. : 5,859,074
DATED : January 12, 1999
INVENTOR(S) : Rezai et al.

It is certified that error appears in the above-identified patent and that said Letters Patent is hereby corrected as shown below:

Column 14,
Line 16, please delete "precrsor" and insert therefor -- precursor --.
Lines 56 and 57, after "water", please delete "," (the comma) and insert therefor--;-- (a semi-colon).

Column 15,
Lines 16 and 18, please delete "precusor" and insert therefor -- precursor --.

Column 16,
Line 41, please delete "35_C." and insert therefor -- 35°C. --.
Line 43, please delete "25_C." and insert therefor -- 25°C. --.
Line 55, please delete "50_C." and insert therefor -- 50°C. --.
Line 66, please delete "205_C." and insert therefor -- 205°C. --.

Column 17,
Lines 1-2, please delete "$200_{13}$C." and insert therefor -- 200°C. --.
Line 35, please delete "precrsor" and insert therefor -- precursor --.

Column 18,
Line 46, please delete "90_" and insert therefor -- 90° --.

Column 20,
Line 48, please delete "50_C." and insert therefor -- 50°C. --.
Line 53, please delete "40_C." and insert therefor -- 40°C. --.

Column 21,
Line 18, please delete "25_" and insert therefor -- 25°C. --.
Line 19, please delete "10_C." and insert therefor -- 10°C. --.
Line 20, please delete "-10_C." and insert therefor-- -10°C. --.
Line 39, please delete "$25_{13}$C." and insert therefor -- 25°C. --.
Line 48, please delete "40_C." and insert therefor -- 40°C. --.

Column 22,
Line 1, please delete "900" and insert therefor -- 90° --.

Column 23,
Line 37, please delete "25_C." and insert therefor -- 25°C. --.
Lines 49 and 58, please delete "$25_{13}$C." and insert therefor -- 25°C. --.

UNITED STATES PATENT AND TRADEMARK OFFICE
CERTIFICATE OF CORRECTION

PATENT NO. : 5,859,074
DATED : January 12, 1999
INVENTOR(S) : Rezai et al.

It is certified that error appears in the above-identified patent and that said Letters Patent is hereby corrected as shown below:

Column 25,
Line 34, before "backsheet", please delete "s".

Column 28,
Line 60, please delete "tranport" and insert therefor -- transport --.

Column 29,
Line 54, please delete "195_C." and insert therefor -- 195°C. --.

Column 30,
Line 45, please delete "0.9≥1.0 g/cc" and insert therefor -- 0.9-1.0 g/cc --.

Column 32,
Lines 7 and 9, please delete "50_C." and insert therefor -- 50°C. --.

Signed and Sealed this

Seventh Day of September, 2004

JON W. DUDAS
*Director of the United States Patent and Trademark Office*